(12) United States Patent
Wu

(10) Patent No.: US 10,775,379 B2
(45) Date of Patent: Sep. 15, 2020

(54) REAGENTS, SYSTEMS AND METHODS FOR ANALYZING WHITE BLOOD CELLS

(71) Applicant: Abbott Laboratories, Abbott Park, IL (US)

(72) Inventor: Jiong Wu, Los Gatos, CA (US)

(73) Assignee: Abbott Laboratories, Abbott Park, IL (US)

( * ) Notice: Subject to any disclaimer, the term of this patent is extended or adjusted under 35 U.S.C. 154(b) by 770 days.

(21) Appl. No.: 14/137,309

(22) Filed: Dec. 20, 2013

(65) Prior Publication Data

US 2014/0273060 A1 Sep. 18, 2014

Related U.S. Application Data

(60) Provisional application No. 61/777,966, filed on Mar. 12, 2013.

(51) Int. Cl.
| | |
|---|---|
| *G01N 33/569* | (2006.01) |
| *G01N 15/14* | (2006.01) |
| *G01N 15/10* | (2006.01) |
| *G01N 15/00* | (2006.01) |

(52) U.S. Cl.
CPC ... *G01N 33/56972* (2013.01); *G01N 15/1434* (2013.01); *G01N 15/1459* (2013.01); *G01N 2015/008* (2013.01); *G01N 2015/0069* (2013.01); *G01N 2015/1006* (2013.01); *G01N 2015/1477* (2013.01); *G01N 2015/1488* (2013.01)

(58) Field of Classification Search
None
See application file for complete search history.

(56) References Cited

U.S. PATENT DOCUMENTS

| | | | |
|---|---|---|---|
| 5,155,044 A | 10/1992 | Ledis et al. | |
| 5,308,772 A | 5/1994 | Sakata et al. | |
| 5,316,725 A | 5/1994 | Carver, Jr. et al. | |
| 5,631,165 A | 5/1997 | Chupp et al. | |
| 5,928,949 A * | 7/1999 | Sakata | G01N 15/1456 436/17 |
| 6,197,593 B1 | 3/2001 | Deka et al. | |
| 2002/0006631 A1 | 1/2002 | Houwen et al. | |
| 2010/0273168 A1 * | 10/2010 | Krockenberger | G01N 15/00 435/6.12 |
| 2011/0275064 A1 * | 11/2011 | Wu | G01N 15/147 435/6.1 |
| 2012/0282598 A1 | 11/2012 | Wu et al. | |
| 2012/0282599 A1 * | 11/2012 | Wu | G01N 15/1434 435/6.1 |
| 2012/0282600 A1 * | 11/2012 | Wu | G01N 15/1459 435/6.1 |

FOREIGN PATENT DOCUMENTS

| | | |
|---|---|---|
| CN | 101311724 | 11/2008 |
| CN | 101750274 | 6/2010 |
| EP | 0136058 | 4/1985 |
| EP | 0525398 | 2/1993 |
| JP | 61-502277 S | 10/1986 |
| JP | 2003-520594 | 7/2003 |
| WO | 2012/088351 | 6/2012 |

OTHER PUBLICATIONS

McCoy et al., Sorting Minor Subpopulations of Cell, Cytometry 12:268-274, 1991.*
AAT-Bioquest, Acridine Orange, Product Sheet, 2008.*
SYTO-MP, SYTO Green Fluorescent Nucleic Acid Stains, Molecular Probes Product Sheet, Jan. 2001.*
SYTO-Dyes, Thermfisher Catalog, Cell-Permeant Cyanine Nucleic Acid Stains, Webpage, 2019 (Year: 2019).*
Groden et al., "Three-Dimensional Pulsatile Flow Simulation Before and After Endovascular Coil Embolization of a Terminal Cerebral Aneurysm," Journal of Cerebral Blood Flow & Metabolism 21(12):1464-1471 (2001).

* cited by examiner

*Primary Examiner* — Louise W Humphrey
*Assistant Examiner* — Srikanth Patury
(74) *Attorney, Agent, or Firm* — Edward J. Baba; Bozicevic, Field & Francis LLP

(57) ABSTRACT

Aspects of the invention include WBC analysis reagents, systems and methods that can be used for analyzing a sample of whole blood to identify, classify, and/or quantify white blood cells (WBC) and WBC sub-populations in the sample. The WBC analysis reagents of the present disclosure generally include at least one membrane-permeable fluorescent dye, a WBC protecting reagent, and a surfactant. In some embodiments, the WBC reagents include a suitable amount of an osmolality adjusting component to adjust the osmolality of the WBC reagent into a desired range.

20 Claims, 32 Drawing Sheets

11.3 µM (1X)

1.13 µM (0.1X)

0.11 μM (0.01X)

0.022 µM (0.002X)

REAGENTS, SYSTEMS AND METHODS FOR ANALYZING WHITE BLOOD CELLS

CROSS-REFERENCE

This application claims the benefit of U.S. Provisional Patent Application No. 61/777,966 filed Mar. 12, 2013, which application is incorporated herein by reference in its entirety.

INTRODUCTION

Accurate counting and classification of white blood cells (WBCs) in whole blood samples using an automated hematology analyzer is an essential diagnostic procedure. WBC analysis is typically achieved by simultaneously lysing red blood cells (RBCs, erythrocytes) and preserving WBCs in a sample of whole blood. One or more WBC reagents are typically needed to perform these functions and to facilitate analysis of WBCs in modern hematology analyzers.

The quality of WBC counting and differentiation is highly dependent on the methods and associated reagents that are used to perform the analysis. Formulating robust WBC analysis reagents has remained one of the top challenges in the hematology industry. In principle, robust WBC reagents result in accurate WBC analysis. Ideally, well-formulated WBC reagents should facilitate (1) thorough lysis of red blood cells (RBCs) under standard conditions, typically in a time frame of approximately 30 seconds or less; (2) breaking or solubilizing large RBC fragments into smaller pieces; and (3) protecting WBCs from the RBC lysis process so that the WBCs can be accurately counted and properly classified.

If a blood sample is insufficiently lysed, then un-lysed RBCs, even at a very small percentages or concentrations, or larger RBC fragments, can interfere with WBC analysis, as it is difficult to separate, or differentiate, RBCs or larger RBC fragments from lymphocytes (the smallest WBCs) using traditional WBC analysis techniques. If the blood sample is over-lysed, then the classification of WBCs may be greatly impacted by excessive damage to the cell membranes of the WBCs. Accordingly, there is a need for improved WBC analysis reagents, systems and methods that can accomplish these objectives.

SUMMARY

Aspects of the invention include WBC analysis reagents, systems and methods that can be used for analyzing a sample of whole blood to identify, classify, and/or quantify white blood cells (WBC) and WBC sub-populations in the sample. The WBC analysis reagents of the present disclosure generally include at least one membrane-permeable fluorescent dye, a WBC protecting reagent, and a surfactant. In some embodiments, the WBC reagents include a suitable amount of an osmolality adjusting component to adjust the osmolality of the WBC reagent into a desired range.

In some embodiments, the present disclosure provides methods for performing a white blood cell (WBC) analysis with an automated hematology analyzer, the methods comprising: (a) diluting a sample of whole blood with a WBC analysis reagent, wherein the WBC analysis reagent comprises: a membrane-permeable fluorescent dye that labels a plurality of nucleus-containing cells in the sample; and an osmolality adjustment component that separates a plurality of WBC subpopulations from one another when analyzed with the hematology analyzer; (b) incubating the diluted blood sample of step (a) for an incubation period of less than about 25 seconds, at a temperature ranging from about 30° C. to about 50° C.; (c) delivering the incubated sample from step (b) to a flow cell in the hematology analyzer; (d) exciting the incubated sample from step (c) with an excitation source as the incubated sample traverses the flow cell; (e) collecting a plurality of light scatter signals and at least one fluorescence emission signal from the excited sample; and (f) performing a WBC differential analysis based on all the signals collected in step (e), while removing from consideration any particles within the diluted blood sample that do not meet a fluorescence threshold based on the at least one fluorescence emission signal.

In some embodiments, the excitation source has a wavelength of from about 350 nm to about 700 nm. In some embodiments, the fluorescence emission signal is collected at a wavelength of from about 360 nm to about 750 nm by a band-pass filter or a long-pass filter. In some embodiments, the membrane-permeable fluorescent dye is acridine orange, hexidium iodide, SYTO RNA Select, SYTO 12 or SYTO 14. In some embodiments, the concentration of the membrane-permeable fluorescent dye in the reagent ranges from about 0.0001% up to about 0.0005%. In some embodiments, the concentration of the membrane-permeable fluorescent dye in the reagent ranges from about 0.01 µM up to about 15 µM. In some embodiments, the osmolality adjustment component is ammonium chloride or sodium chloride. In some embodiments, the concentration of the osmolality adjustment component ranges from about 0.1% up to about 0.5%. In some embodiments, the reagent further comprises a WBC protecting agent. In some embodiments, the WBC protecting agent is formaldehyde, glutaraldehyde, butoxyethanol, phenoxyethanol, or isopropyl alcohol. In some embodiments, the concentration of the WBC protecting agent ranges from about 0.1% up to about 1.0%. In some embodiments, the WBC analysis reagent further comprises a surfactant. In some embodiments, the surfactant is saponin. In some embodiments, the concentration of the surfactant ranges from about 0.01% up to about 0.05%. In some embodiments, the reagent further comprises a pH buffering component. In some embodiments, the pH buffering component is sodium acetate or sodium bicarbonate. In some embodiments, the concentration of the pH buffering component ranges from about 0.01% up to about 0.5%. In some embodiments, the reagent further comprises an antimicrobial agent. In some embodiments, the antimicrobial agent is proclin. In some embodiments, the concentration of the antimicrobial agent ranges from about 0.01% up to about 0.1%. In some embodiments, the pH of the WBC analysis reagent ranges from about 2.5 up to about 12.5 pH units. In some embodiments, the osmolality of the WBC analysis reagent ranges from about 25 up to about 350 mOsm.

In some embodiments, the present disclosure provides systems for conducting a white blood cell (WBC) differential analysis on a sample of whole blood, the systems comprising: (a) a hematology analyzer, the hematology analyzer comprising: an excitation source positioned to excite particles within the blood sample; a plurality of detectors including (1) an axial light loss detector positioned to measure axial light loss from the excited blood sample, (2) an intermediate angle scatter detector positioned to measure intermediate angle scatters from the excited blood sample, (3) a polarized side scatter detector positioned to measure large angle polarized side scatters from the excited blood sample, (4) a depolarized side scatter detector positioned to measure large angle depolarized side scatter from the excited blood sample, and (5) a fluorescence detector positioned to measure fluorescence emitted from the excited blood sample; and a processor configured to: (I) receive the measurements of (1) axial light loss, (2) intermediate angle scatters, (3) large angle polarized side scatters, (4) large angle depolarized side scatters, and (5) fluorescence from the plurality of detectors, and (II) perform a WBC differential analysis of the blood sample, based on all five measurements, for particles that emit fluorescence above a fluorescence threshold; and (b) a reagent for analyzing WBCs in the sample, the reagent comprising: a membrane-permeable fluorescent dye; and an osmolality adjustment component; wherein the concentration of the membrane-permeable fluorescent dye is sufficient to facilitate identification of one or more cells in the sample that contain a nucleus using the hematology analyzer; and wherein the concentration of the osmolality adjustment component is sufficient to facilitate identification of a plurality of subpopulations of WBCs in the sample using the hematology analyzer.

In some embodiments, the membrane-permeable fluorescent dye is acridine orange, hexidium iodide, SYTO RNA Select, SYTO 12 or SYTO 14. In some embodiments, the concentration of the membrane-permeable fluorescent dye in the reagent ranges from about 0.0001% up to about 0.0005%. In some embodiments, the concentration of the membrane-permeable fluorescent dye in the reagent ranges from about 0.01 µM up to about 15 µM. In some embodiments, the osmolality adjustment component is ammonium chloride or sodium chloride. In some embodiments, the concentration of the osmolality adjustment component ranges from about 0.1% up to about 0.5%. In some embodiments, the reagent further comprises a WBC protecting agent. In some embodiments, the WBC protecting agent is formaldehyde, glutaraldehyde, butoxyethanol, phenoxyethanol, or isopropyl alcohol. In some embodiments, the concentration of the WBC protecting agent ranges from about 0.1% up to about 1.0%. In some embodiments, the reagent further comprises a surfactant. In some embodiments, the surfactant is saponin. In some embodiments, the concentration of the surfactant ranges from about 0.01% up to about 0.05%. In some embodiments, the reagent further comprises a pH buffering component. In some embodiments, the pH buffering component is sodium acetate or sodium bicarbonate. In some embodiments, the concentration of the pH buffering component ranges from about 0.01% up to about 0.5%. In some embodiments, the reagent further comprises an antimicrobial agent. In some embodiments, the antimicrobial agent is proclin. In some embodiments, the concentration of the antimicrobial agent ranges from about 0.01% up to about 0.1%. In some embodiments, the pH of the reagent ranges from about 2.5 up to about 12.5 pH units. In some embodiments, the osmolality of the reagent ranges from about 25 up to about 350 mOsm.

In some embodiments, the processor is further configured to pre-screen the received measurements to remove from consideration any particles that do not meet the fluorescence threshold. In some embodiments, the axial light loss detector measures axial light loss at 0° scatter. In some embodiments, the intermediate angle scatter detector measures light angle scatter at about 3° to about 15°. In some embodiments, the plurality of detectors includes one or more photomultiplier tubes. In some embodiments, the excitation source is a laser. In some embodiments, the laser emits light at a wavelength corresponding to the fluorescent dye. In some embodiments, the fluorescent dye is selected to correspond with the excitation source.

In some embodiments, the system further comprises an incubation subsystem for diluting the blood sample with the reagent. In some embodiments, the incubation subsystem is configured to incubate the blood sample with the reagent for a period of time that is less than about 25 seconds. In some embodiments, the incubation subsystem is configured to incubate the blood sample with the reagent for a period of time that is less than about 17 seconds. In some embodiments, the incubation subsystem is configured to incubate the blood sample with the reagent for a period of time that is less than about 9 seconds. In some embodiments, the incubation subsystem is configured to incubate the blood sample with the reagent at a temperature ranging from about 30° C. to about 50° C. In some embodiments, the incubation subsystem is configured to incubate the blood sample with the reagent at a temperature of about 40° C.

In some embodiments, the present disclosure provides reagents for analyzing white blood cells (WBCs) in a sample of whole blood using a hematology analyzer, the reagents comprising: a membrane-permeable fluorescent dye in a sufficient concentration to facilitate identification of a plurality of cells in the sample that contain a nucleus using the hematology analyzer; and an osmolality adjustment component in a sufficient concentration to facilitate identification of a plurality of subpopulations of WBCs in the sample using the hematology analyzer.

In some embodiments, the membrane-permeable fluorescent dye is acridine orange, hexidium iodide, SYTO RNA Select, SYTO 12 or SYTO 14. In some embodiments, the concentration of the membrane-permeable fluorescent dye in the reagent ranges from about 0.0001% up to about 0.0005%. In some embodiments, the concentration of the membrane-permeable fluorescent dye in the reagent ranges from about 0.01 µM up to about 15 µM. In some embodiments, the osmolality adjustment component is ammonium chloride or sodium chloride. In some embodiments, the concentration of the osmolality adjustment component ranges from about 0.1% up to about 0.5%. In some embodiments, the reagent further comprises a WBC protecting agent. In some embodiments, the WBC protecting agent is formaldehyde, glutaraldehyde, butoxyethanol, phenoxyethanol, or isopropyl alcohol. In some embodiments, the concentration of the WBC protecting agent ranges from about 0.1% up to about 1.0%. In some embodiments, the WBC analysis reagent further comprises a surfactant. In some embodiments, the surfactant is saponin. In some embodiments, the concentration of the surfactant ranges from about 0.01% up to about 0.05%.

In some embodiments, the reagent further comprises a pH buffering component. In some embodiments, the pH buffering component is sodium acetate or sodium bicarbonate. In some embodiments, the concentration of the pH buffering component ranges from about 0.01% up to about 0.5%. In some embodiments, the reagent further comprises an antimicrobial agent. In some embodiments, the antimicrobial agent is proclin. In some embodiments, the concentration of the antimicrobial agent ranges from about 0.01% up to about 0.1%. In some embodiments, the pH of the WBC analysis reagent ranges from about 2.5 up to about 12.5 pH units. In some embodiments, the osmolality of the WBC analysis reagent ranges from about 25 up to about 350 mOsm.

BRIEF DESCRIPTION OF THE FIGURES

The accompanying figures, which are incorporated herein, form part of the specification. Together with this written description, the figures further serve to explain the principles of, and to enable a person skilled in the relevant art(s), to make and use the reagents, systems and methods presented herein. In the figures, like reference numbers indicate identical or functionally similar elements.

DETAILED DESCRIPTION

Figure 1:
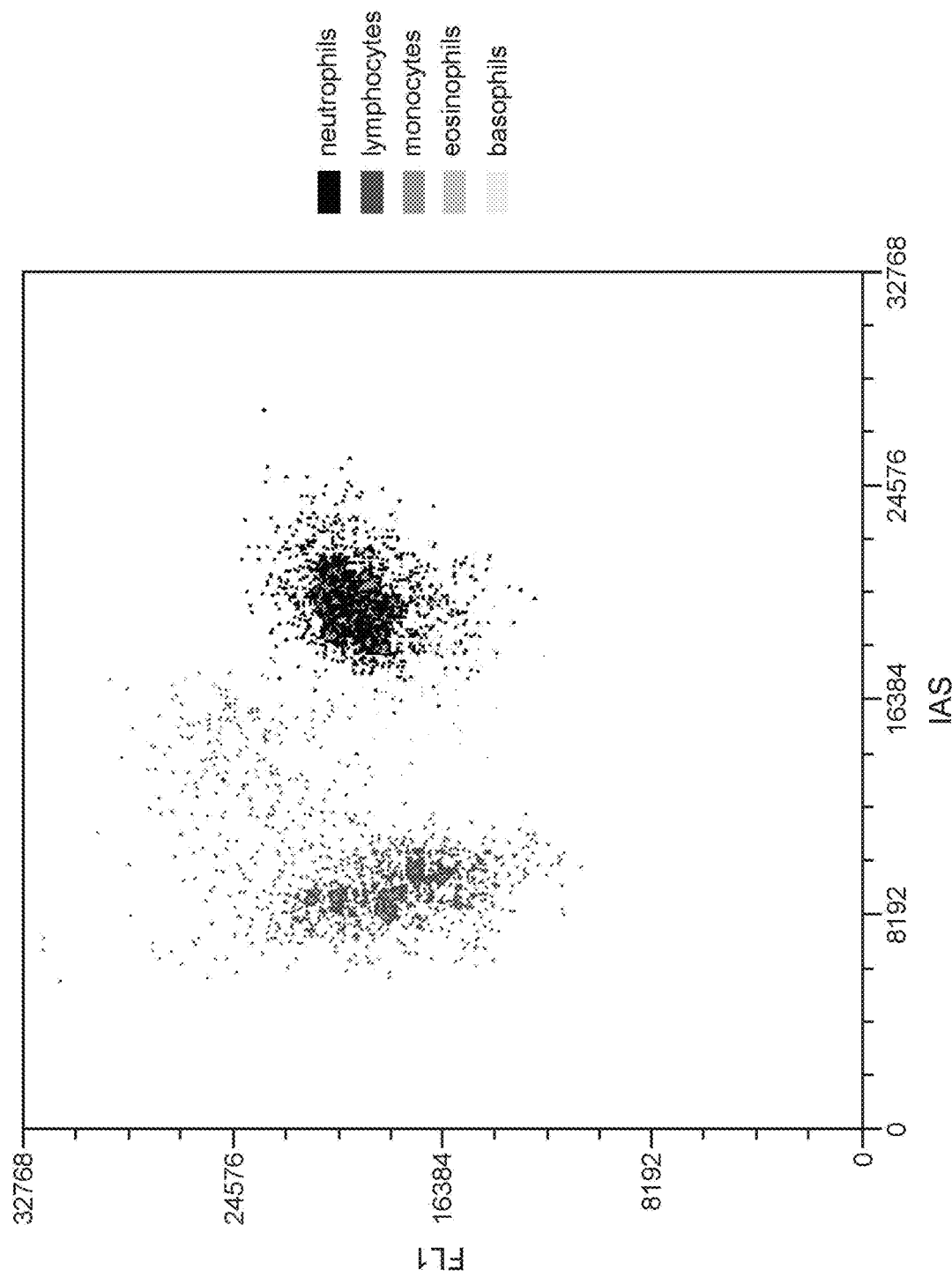
FIG. 1 shows a WBC scattergram (FL1 vs. IAS) that was obtained using a WBC analysis reagent containing 3.8 μM acridine orange as the fluorescent dye. Neutrophils, lymphocytes, monocytes, eosinophils, and basophils are shown in the scattergram.
Figure 2:
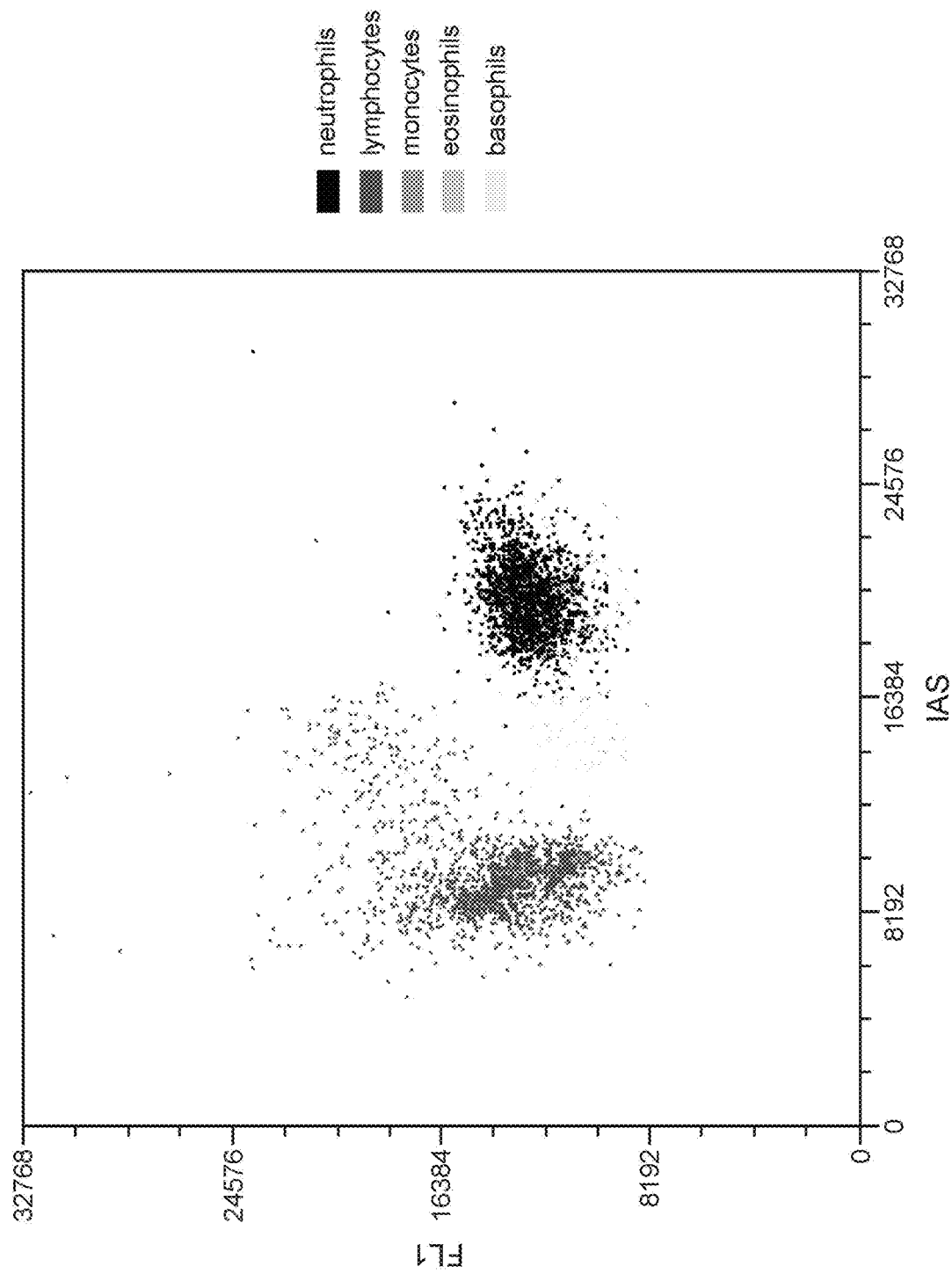
FIG. 2 shows a WBC scattergram (FL1 vs. IAS) that was obtained using a WBC analysis reagent containing 1.3 μM hexidium iodide as the fluorescent dye. Neutrophils, lymphocytes, monocytes, eosinophils, and basophils are shown in the scattergram.
Figure 3:
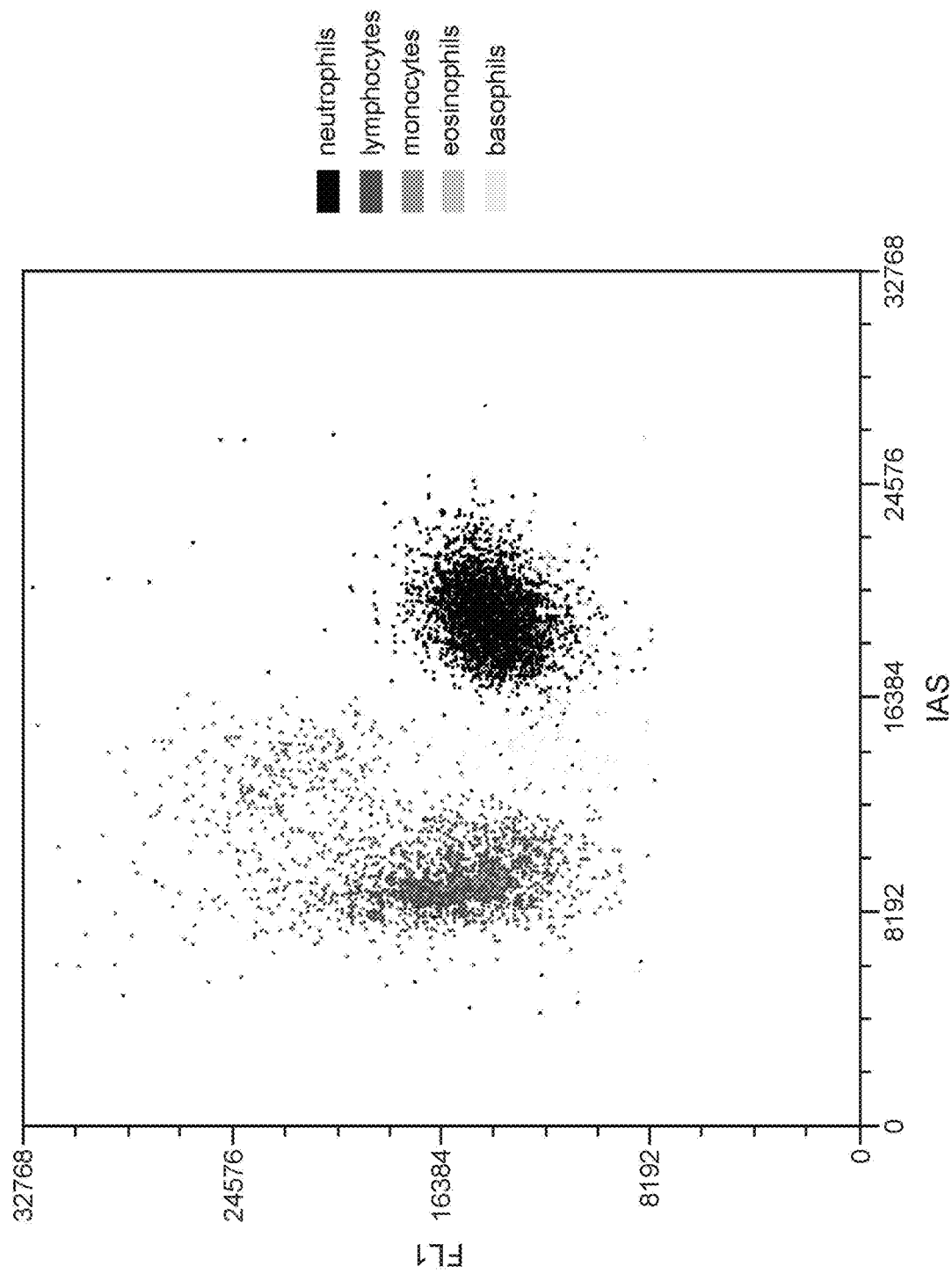
FIG. 3 shows a WBC scattergram (FL1 vs. IAS) that was obtained using a WBC analysis reagent containing 1.3 μM SYTO RNA Select as the fluorescent dye. Neutrophils, lymphocytes, monocytes, eosinophils, and basophils are shown in the scattergram.
Figure 4:
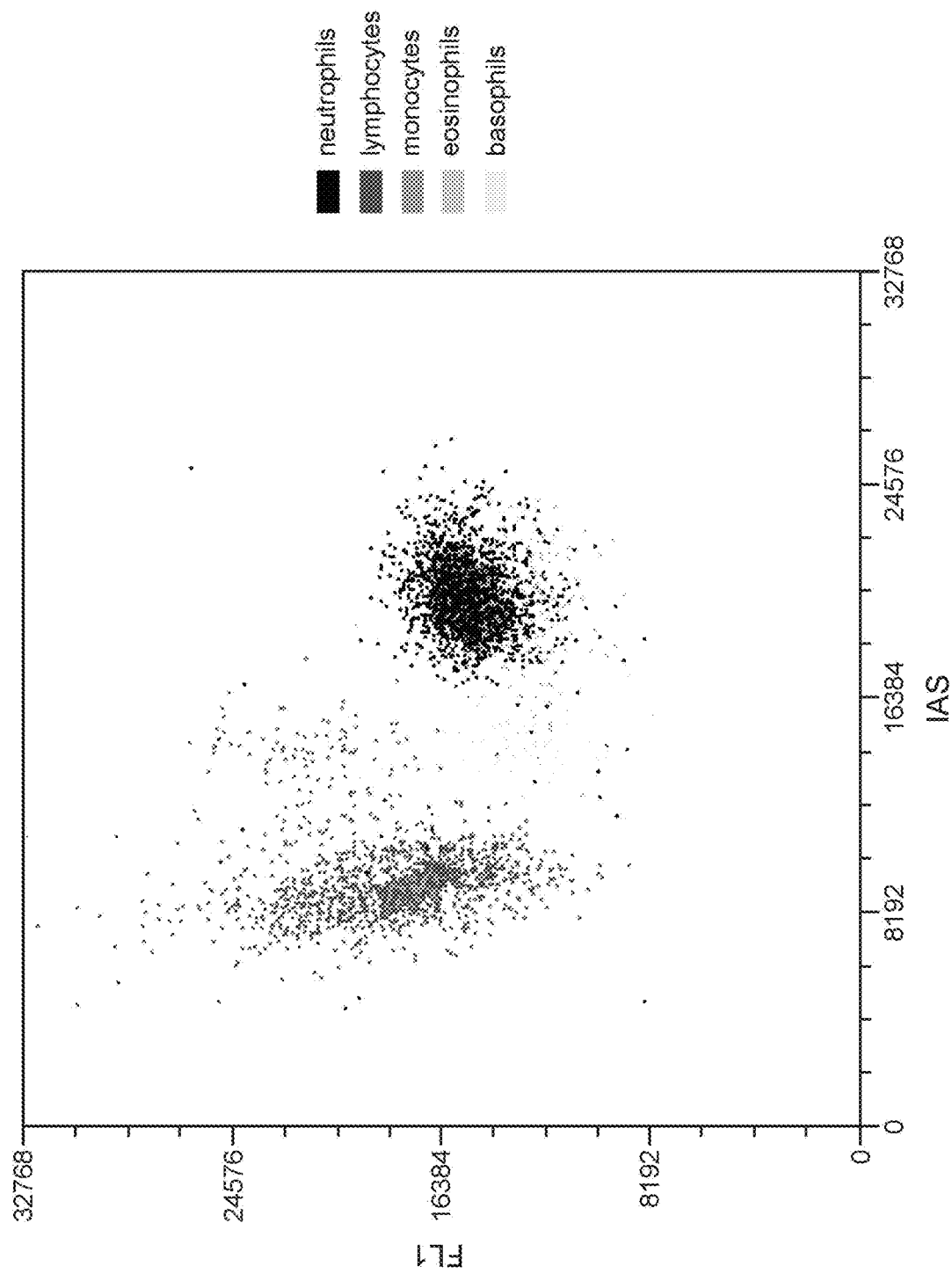
FIG. 4 shows a WBC scattergram (FL1 vs. IAS) that was obtained using a WBC analysis reagent containing 1.3 μM SYTO 12 as the fluorescent dye. Neutrophils, lymphocytes, monocytes, eosinophils, and basophils are shown in the scattergram.
Figure 5:
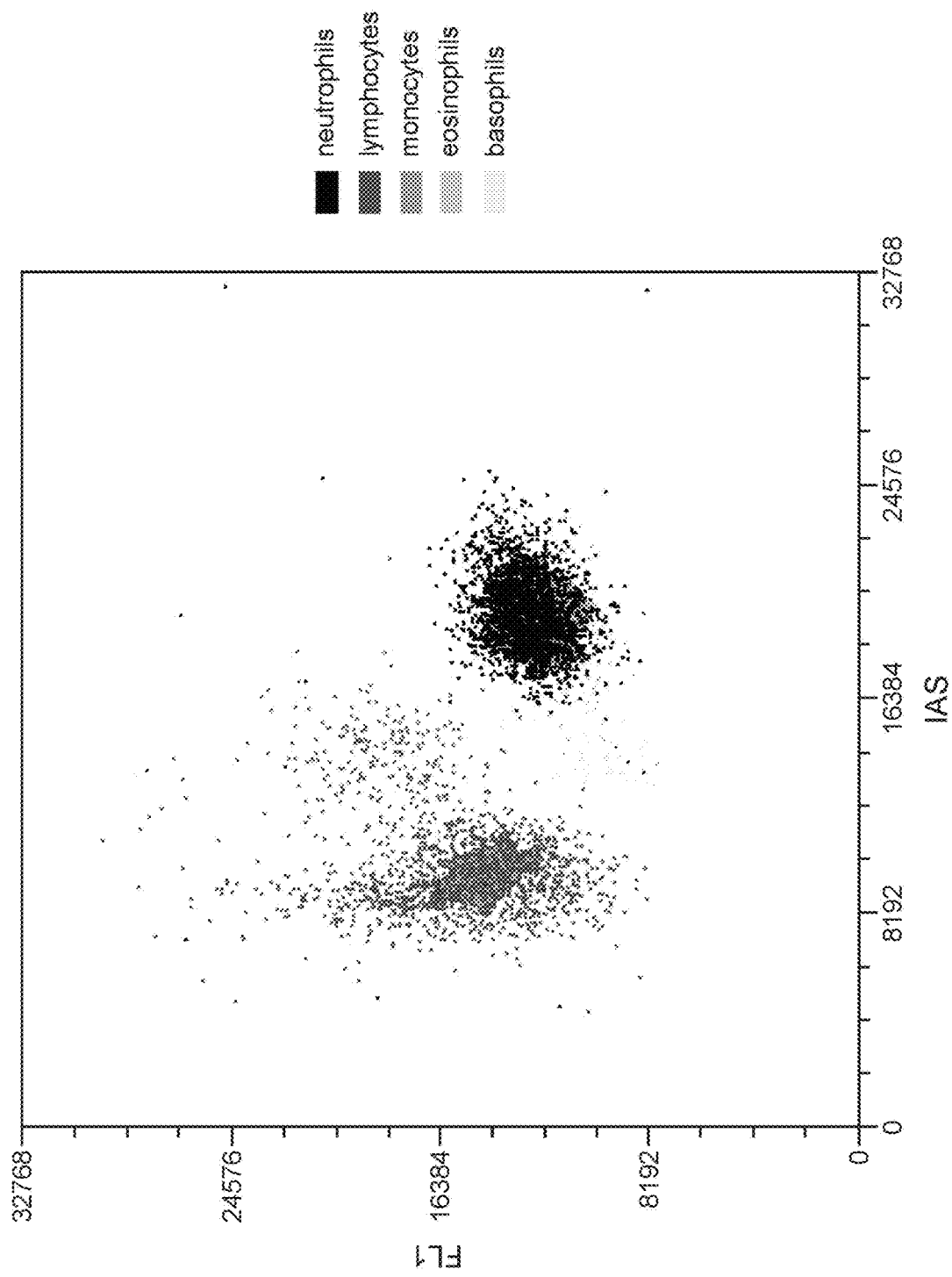
FIG. 5 shows a WBC scattergram (FL1 vs. IAS) that was obtained using a WBC analysis reagent containing 1.3 μM SYTO 14 as the fluorescent dye. Neutrophils, lymphocytes, monocytes, eosinophils, and basophils are shown in the scattergram.
Figure 6A:
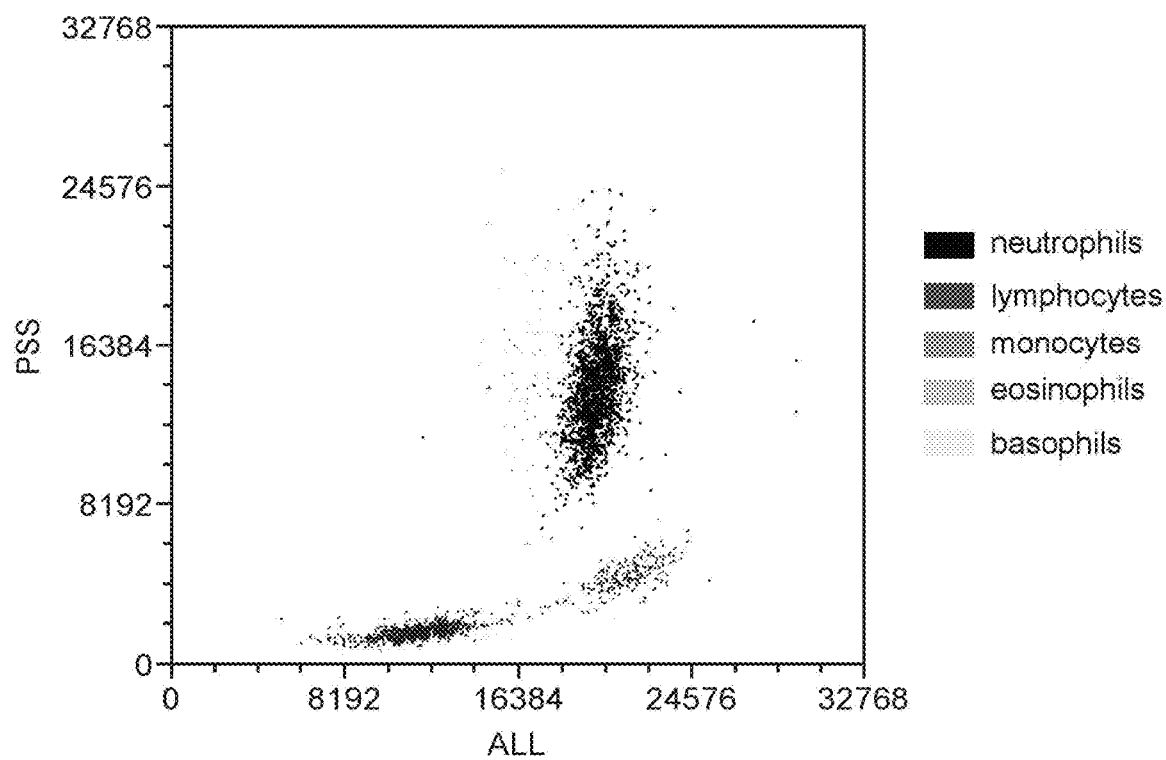
FIG. 6A shows two WBC scattergrams (PSS vs. ALL and FL1 vs. IAS) that were obtained using a WBC analysis reagent containing acridine orange as the fluorescent dye at a concentration of 11.3 μM (1×). Neutrophils, lymphocytes, monocytes, eosinophils, and basophils are shown in the scattergrams.
Figure 6A:
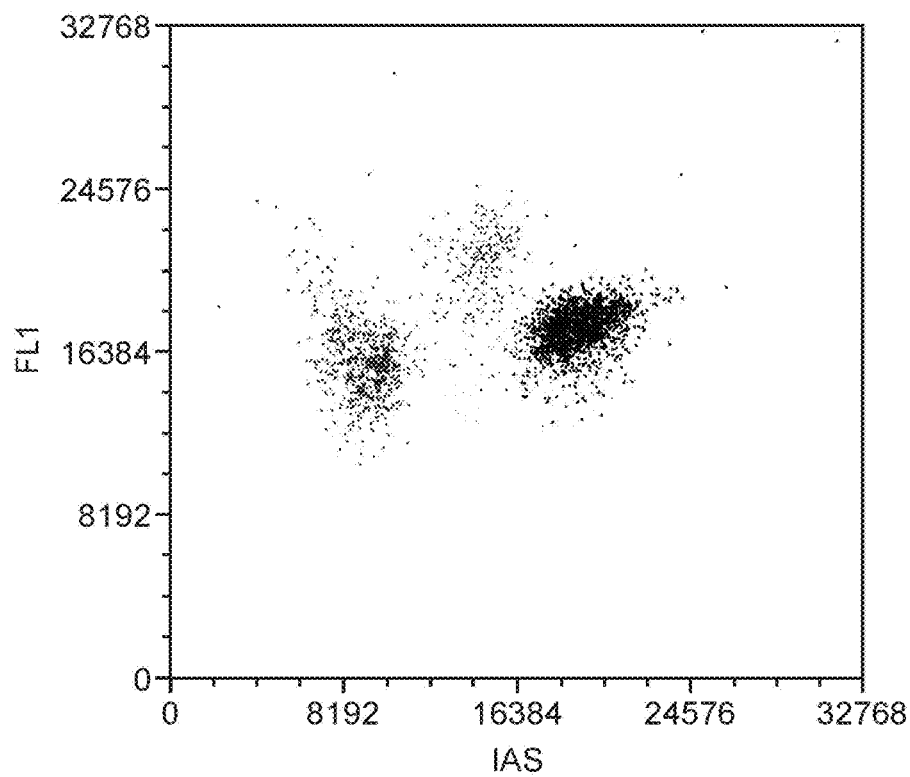
Figure 6B:
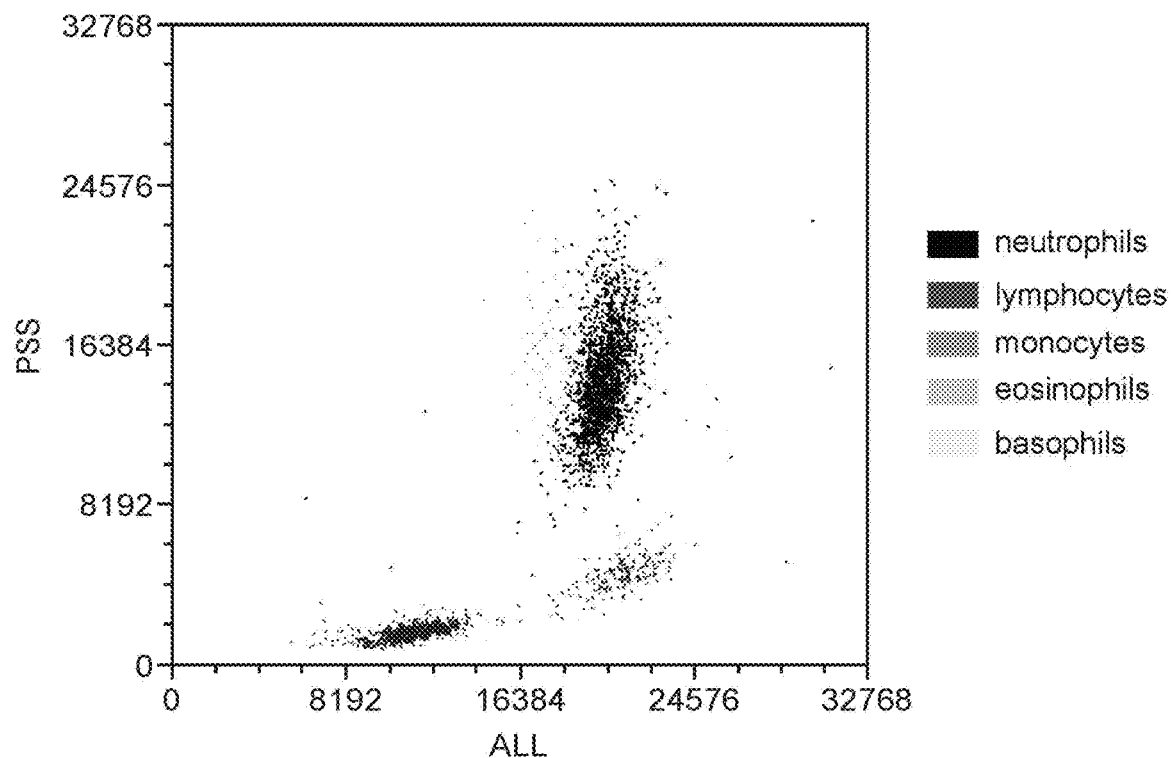
FIG. 6B shows two WBC scattergrams (PSS vs. ALL and FL1 vs. IAS) that were obtained using a WBC analysis reagent containing acridine orange as the fluorescent dye at a concentration of 1.13 μM (0.1×). Neutrophils, lymphocytes, monocytes, eosinophils, and basophils are shown in the scattergrams.
Figure 6B:
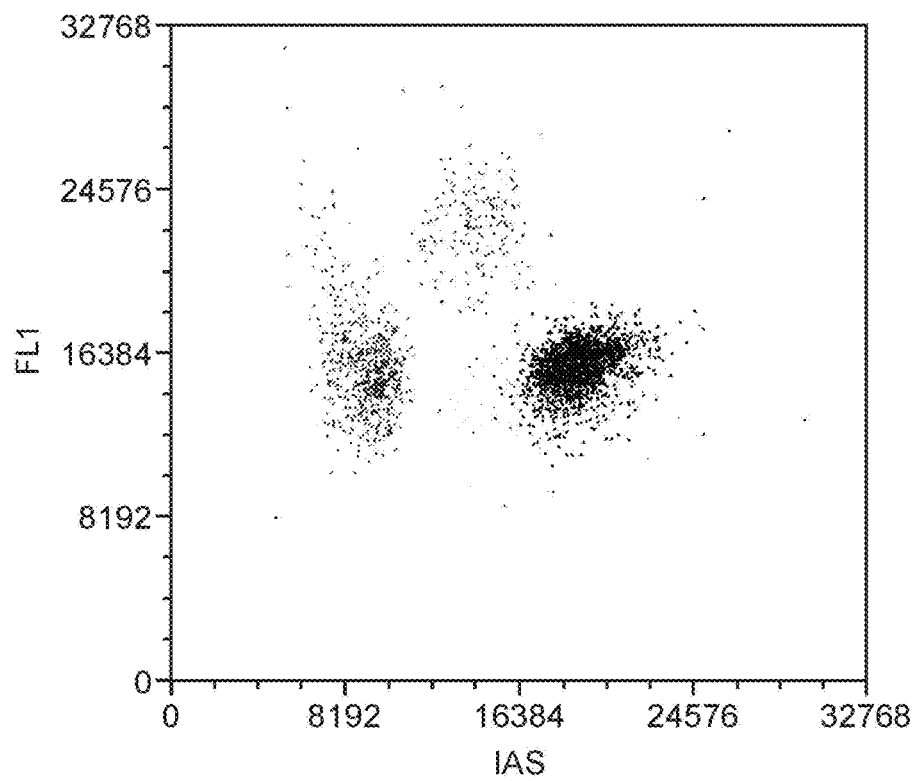
Figure 6C:
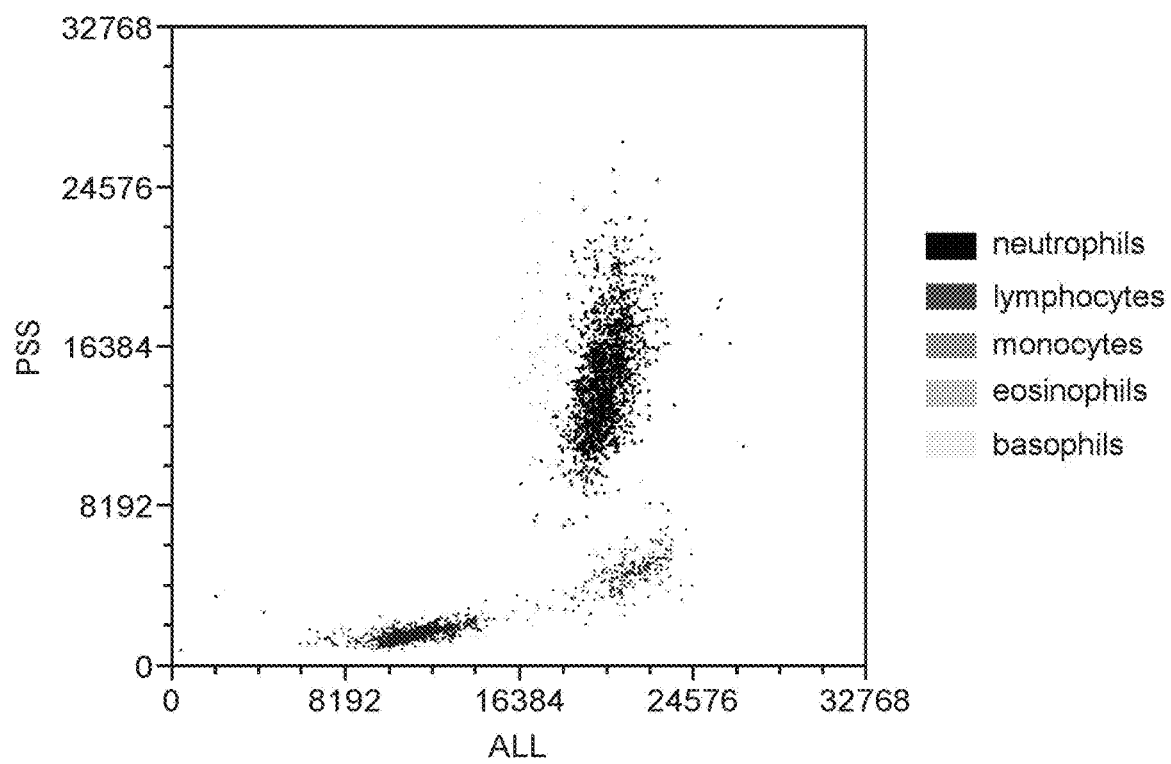
FIG. 6C shows two WBC scattergrams (PSS vs. ALL and FL1 vs. IAS) that were obtained using a WBC analysis reagent containing acridine orange as the fluorescent dye at a concentration of 0.11 μM (0.01×). Neutrophils, lymphocytes, monocytes, eosinophils, and basophils are shown in the scattergrams.
Figure 6C:
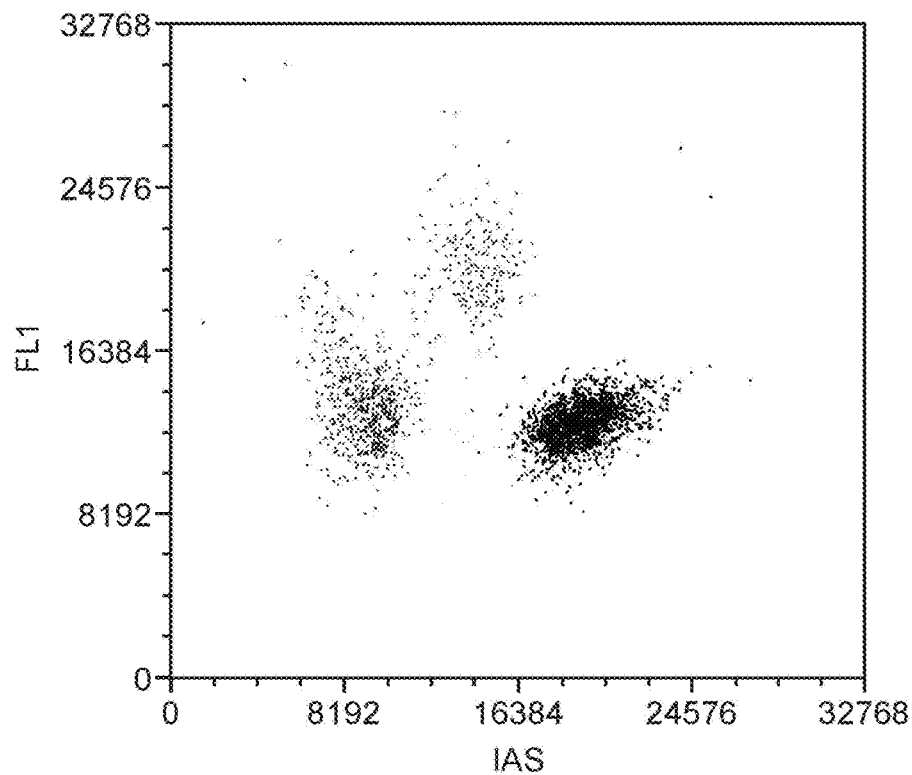
Figure 6D:
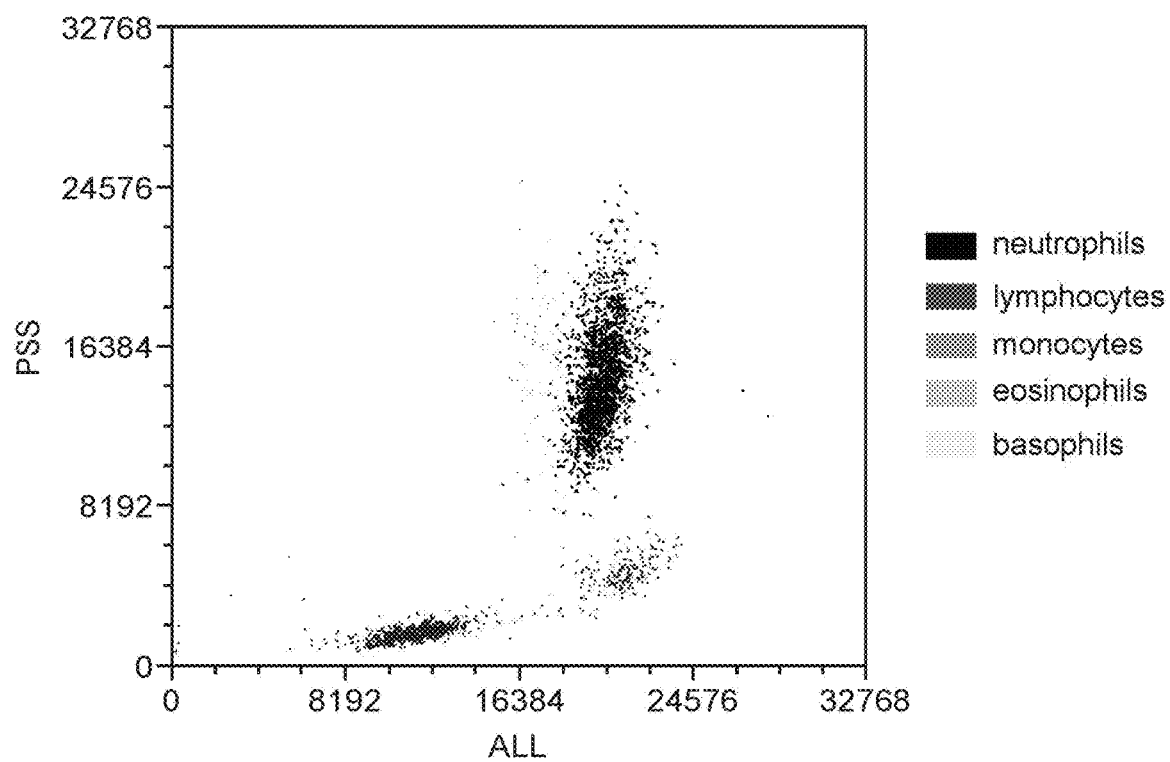
FIG. 6D shows two WBC scattergrams (PSS vs. ALL and FL1 vs. IAS) that were obtained using a WBC analysis reagent containing acridine orange as the fluorescent dye at a concentration of 0.022 μM (0.002×). Neutrophils, lymphocytes, monocytes, eosinophils, and basophils are shown in the scattergrams.
Figure 6D:
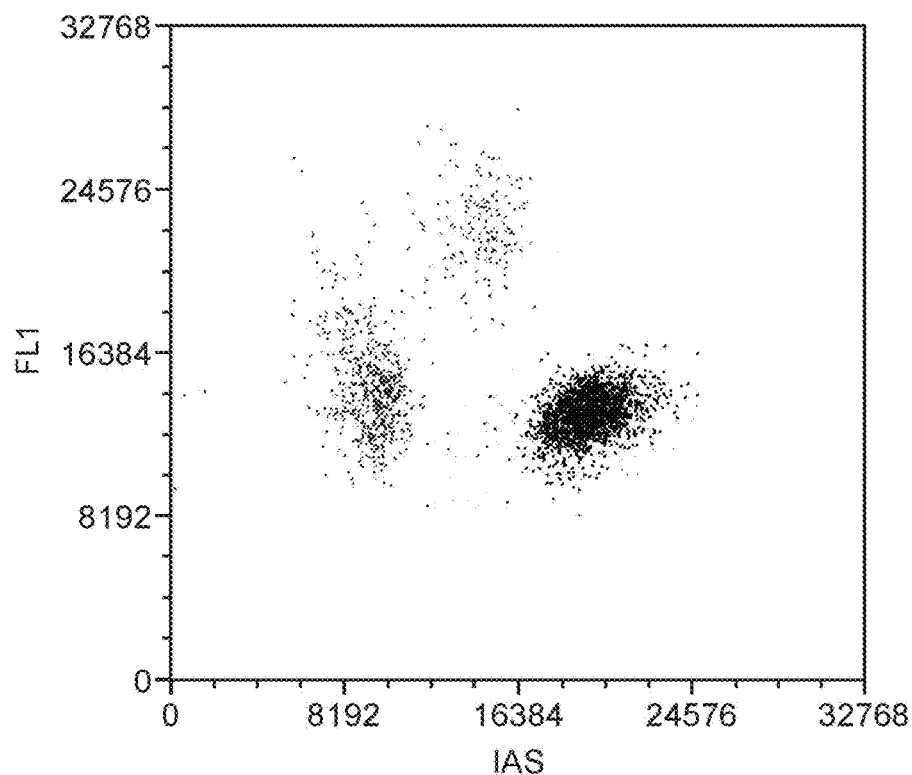

Aspects of the invention include WBC analysis reagents, systems and methods that can be used for analyzing a sample of whole blood to identify, classify, and/or quantify white blood cells (WBC) and WBC sub-populations in the sample. The WBC analysis reagents of the present disclosure generally include at least one membrane-permeable fluorescent dye, a WBC protecting reagent, and a surfactant. In some embodiments, the WBC reagents include a suitable amount of an osmolality adjusting component to adjust the osmolality of the WBC reagent into a desired range.

In some aspects, the reagents, systems and methods disclosed herein are used to screen WBCs using a fluorescence staining and fluorescence triggering strategy. By using this approach, interference from unlysed RBCs (e.g., lysis-resistant RBCs, or "rstRBCs") and RBC fragments is substantially or completely eliminated, thereby ensuring accurate counting and differentiation of WBCs and WBC sub-populations. The present disclosure also provides WBC analysis reagents that facilitate enhanced analysis of WBCs using, e.g., an automated hematology analyzer that is configured to carry out the fluorescence triggering approach. The WBC analysis reagents of the present disclosure are also suitable for assays of samples containing fragile lymphocytes (or other fragile WBCs), including aged samples.

In some embodiments, for example, the methods disclosed herein involve: contacting a blood sample with a WBC analysis reagent that includes at least one membrane-permeable fluorescent dye, a WBC protecting reagent, a surfactant, and an osmolality adjustment component in a concentration that is sufficient to separate WBC subpopulations on a scattergram generated by a hematology analyzer; incubating the blood sample with the WBC analysis reagent at an elevated temperature; staining the blood sample with the fluorescent dye; using a fluorescence trigger on a hematology analyzer to screen the blood sample for WBCs; and using a combination of measurements of (1) axial light loss, (2) intermediate angle scatters, (3) large angle polarized side scatter, (4) large angle depolarized side scatter, and (5) fluorescence emission to perform a differential analysis of WBCs in the sample (e.g., counting the number of each of a variety of subtypes or sub-populations of WBCs that are present in the sample).

Use of the fluorescent dyes described herein in combination with the fluorescence trigger analysis approach described herein provides exceptional sensitivity in the analysis of WBCs by screening out RBCs that have not been lysed by the WBC reagent. This in turn facilitates the use of more gentle WBC analysis reagents (e.g., analysis reagents that don't lyse or damage WBCs in the process of lysing RBCs in the sample), which can be finely tuned to facilitate further separation of various subpopulations of WBCs from one another (as viewed on one or more scattergrams generated by a hematology analyzer) using, e.g., osmolality adjustment components.

As used herein, the term "fluorescence information" means data collected from a fluorescence channel of a hematology analyzer. As used herein, the term "fluorescence channel" means a detection device, such as a photomultiplier tube, set at an appropriate wavelength band for measuring the quantity of fluorescence emitted from a sample.

WBC Analysis Reagents

Aspects of the invention include WBC analysis reagents that can be used to enhance the analysis of WBCs and WBC sub-populations in a blood sample using an automated hematology analyzer. WBC analysis reagents in accordance with embodiments of the invention are generally used to lyse RBCs in the blood sample, while at the same time preserving WBCs in the blood sample for analysis. WBC analysis reagents in accordance with embodiments of the invention also generally provide enhanced, interference-free separation of WBC subpopulations from one another when viewed on a differential scattergram produced by a hematology analyzer. This enhanced separation facilitates more accurate analysis of the various WBC subpopulations that are present within the blood sample.

WBC analysis reagents in accordance with embodiments of the invention may generally include at least one membrane-permeable fluorescent dye, a WBC protecting reagent, a surfactant, an osmolality adjustment component, as well as several additional components. Each of these components is described in further detail below.

Membrane-Permeable Fluorescent Dyes

Membrane-permeable fluorescent dyes may be used to differentiate two classes of blood cells; namely, blood cells containing DNA and blood cells that do not contain DNA.

Since WBCs contain large amounts of DNA in their nuclei and RBCs do not, inclusion of a membrane-permeable fluorescent dye that interacts with DNA facilitates differentiation of WBCs from RBCs. The purpose of the dye is to pass through the cell membrane, bind to one or more nucleic acids with sufficient affinity, and emit a fluorescent signal with adequate Stokes shift when the dye is excited by an appropriate source of light. The peak absorption of the dye in the visible band substantially matches the wavelength of the source of light (within 50 nm of the wavelength of the source of light, more preferably, within 25 nm of the wavelength of the source of light), in order to properly excite the dye and achieve optimal results.

The membrane-permeable fluorescent dye is preferably: 1) capable of binding to nucleic acids (e.g., DNA), 2) capable of penetrating the cell membranes of WBCs, 3) excitable at a selected wavelength when subjected to a source of light, 4) emits fluorescence upon excitation by the source of light, and 5) is biostable and soluble in a liquid (e.g., an aqueous solution). Examples of suitable membrane-permeable fluorescent dyes include but are not limited to: acridine orange, hexidium iodide, SYTO 12, SYTO 14, SYTO RNA Select, or any equivalents thereof.

The fluorescent dye is generally used to activate WBCs and screen out unlysed RBCs and fragments of RBCs based on a fluorescence trigger configured in the hematology analyzer. In some embodiments, the dye is present at a concentration of from about 1 pg/L up to about 1 mg/L, depending on the binding affinity, membrane penetration characteristics, and/or the intensity of fluorescence emission of the dye. In some embodiments, the dye is present at a concentration of from about 1 µM up to about 1 mM, depending on the binding affinity, membrane penetration characteristics, and/or the intensity of fluorescence emission of the dye. While various dyes are available, the dye selected is generally paired with the excitation source of the hematology analyzer such that one single dye is used to stain and excite fluorescence emission in all WBC sub-populations intended to be identified, quantified, and/or analyzed. As such, in some embodiments a single (i.e., exclusive) dye can be used to identify, quantify, and analyze all of the different WBC subpopulations that are present in the sample at the same time. In some embodiments, more than one fluorescent dye may be included in the WBC analysis reagent.

In some embodiments, a fluorescent dye is present in a WBC analysis reagent at a concentration of about 1.0 µM, up to about 1.3 µM, up to about 1.5 µM, up to about 1.8 µM, or up to about 2.0 µM or more. In some embodiments, a fluorescent dye is present in a WBC analysis reagent at a concentration of about 0.0001%, up to about 0.0002%, up to about 0.0003%, up to about 0.0004%, or up to about 0.0005% or more. In certain embodiments, a fluorescent dye is present in a WBC analysis reagent at a concentration of about 0.01 µM, up to about 0.022 µM, up to about 0.05 µM, up to about 0.1 µM, up to about 0.11 µM, up to about 0.5 µM, up to about 1.0 µM, up to about 1.13 µM, up to about 5.0 µM, up to about 10 µM, up to about 11.3 µM, up to about 15 µM or more.

WBC Protecting Agents

WBC analysis reagents in accordance with some embodiments of the invention may include a WBC protecting agent that prevents excessive damage to WBCs during RBC lysis. Examples of WBC protecting reagents include, but are not limited to, formaldehyde, glutaraldehyde, butoxyethanol, phenoxyethanol, isopropyl alcohol, or combinations thereof. In some embodiments, a WBC protecting agent is present in a WBC analysis reagent at a concentration of about 0.1%, up to about 0.2%, up to about 0.3%, up to about 0.4%, up to about 0.5%, up to about 0.6%, up to about 0.7%, up to about 0.8%, up to about 0.9%, or up to about 1%.

Osmolality Adjustment Components

WBC analysis reagents in accordance with embodiments of the invention may include an osmolality adjustment component. Osmolality adjustment components are generally reagents that change the osmolality of the WBC analysis reagent to a desired extent. Examples of osmolality adjustment components include, but are not limited to: salts containing cations, such as, e.g., Na+, K+, NH4+, Ca2+, and Mg2+-containing salts; salts containing anions, such as, e.g., Cl−, Br−, NO3−, CO32−, HCO3−, SO42−, HSO4−, PO43−, HPO42−, H2PO4−, COOH−, and CH3COO−-containing salts; organic compounds, such as, e.g., sugars (e.g., glucose and sucrose) and alcohols (e.g., ethanol and methanol); or equivalents thereof.

In some embodiments, an osmolality adjustment component is present in a WBC analysis reagent at a concentration of about 0.1% or more, up to about 0.125% or more, up to about 0.25% or more, up to about 0.5% or more.

Additional Components

In addition to the components described above, WBC analysis reagents in accordance with some embodiments of the invention may also include a variety of additional components. For example, in some embodiments, a WBC analysis reagent may include a buffer or salt that is used to adjust and/or maintain the pH of the solution and to achieve optimal osmolality of the reagent. Examples of buffers or salts include, but are not limited to sodium acetate, sodium bicarbonate, or combinations thereof. In some embodiments, a buffer or salt may be present in a WBC analysis reagent at a concentration of about 0.01%, up to about 0.02%, up to about 0.03%, up to about 0.04%, up to about 0.05%, up to about 0.06%, up to about 0.07%, up to about 0.08%, up to about 0.09%, up to about 0.1%, up to about 0.15%, up to about 0.2%, up to about 0.25%, up to about 0.3%, up to about 0.35%, up to about 0.4%, up to about 0.45%, up to about 0.5% or more.

In some embodiments, a WBC analysis reagent may have a pH that varies from about 2.5 pH units, up to about 3.0 pH units, up to about 3.5 pH units, up to about 4.0 pH units, up to about 4.5 pH units, up to about 5.0 pH units, up to about 5.5 pH units, up to about 6.0 pH units, up to about 6.5 pH units, up to about 7.0 pH units, up to about 7.5 pH units, up to about 8.0 pH units, up to about 8.5 pH units, up to about 9.0 pH units, up to about 9.5 pH units, up to about 10 pH units, up to about 10.5 pH units, up to about 11 pH units, up to about 11.5 pH units, up to about 12 pH units, up to about 12.5 pH units.

In certain embodiments, a WBC analysis reagent may include an antimicrobial agent that is used to prevent microbial growth in the WBC analysis reagent. Examples of antimicrobial agents include, but are not limited to, Proclins, e.g., Proclin 300 or equivalents thereof. The concentration of the antimicrobial agent is generally sufficient to preserve the WBC analysis reagent for the shelf life required. In some embodiments, an antimicrobial agent may be present in a WBC analysis reagent at a concentration of about 0.01%, up to about 0.02%, up to about 0.03%, up to about 0.04%, up to about 0.05%, up to about 0.06%, up to about 0.07%, up to about 0.08%, up to about 0.09%, or up to about 0.1% or more.

In some embodiments, a WBC analysis reagent may include a surfactant that is used to minimize the accumulation of RBC fragments and prevent RBC fragments from interfering with the analysis of WBCs in the sample.

Examples of surfactants include, but are not limited to, saponin, or equivalents thereof. In some embodiments, a surfactant may be present in a WBC analysis reagent at a concentration of about 0.01%, up to about 0.015%, up to about 0.02%, up to about 0.025%, up to about 0.03%, up to about 0.035%, up to about 0.04%, up to about 0.045%, up to about 0.05% or more.

In some embodiments, a WBC analysis reagent may include an RBC lysing component. RBC lysing components may generally help to lyse RBCs in a blood sample while also contributing to the osmolality adjustment of the WBC analysis reagent to facilitate separation and/or analysis of different classes of WBCs present in the sample. Examples of RBC lysing components include, but are not limited to: ammonium salts, such as, e.g., ammonium chloride; tertiary ammonium salts; quaternary ammonium salts; or equivalents thereof.

Methods of Preparation of Wbc Analysis Reagents

In some embodiments, a WBC analysis reagent is prepared using a two-stage preparation process to dissolve the membrane-permeable fluorescent dye. In the first step, the fluorescent dye is dissolved in a suitable organic solvent, e.g., DMSO, to create a solution that contains the fluorescent dye at a suitable first concentration. In the second step, the solution containing the fluorescent dye in the organic solvent is mixed with an aqueous solvent to create an aqueous WBC analysis reagent that contains the fluorescent dye at the desired final concentration. In some embodiments, the aqueous solvent may contain additional components of the WBC analysis reagent.

Methods of Lysing RBCs in a Blood Sample

WBC analysis reagents in accordance with embodiments of the invention may generally be used to lyse RBCs in a sample of whole blood. Lysis of RBCs in a blood sample can be conducted at a temperature above room temperature (e.g., between about 30° C. to about 50° C., such as about 40° C.) over a period of time ranging from about 5 seconds up to about 1 minute. In some embodiments, lysis of RBCs can be carried out in a relatively short amount of time (e.g., less than about 25 seconds, less than about 17 seconds, or even less than about 9 seconds), following mixing of a sample of blood with a WBC analysis reagent. The dilution ratio of the volume of the blood sample to the volume of the WBC analysis reagent (expressed as "volume of blood sample: volume of WBC analysis reagent") can vary greatly. In some embodiments, the ratio of the volume of the blood sample to the volume of the WBC analysis reagent ranges from about 1:10, up to about 1:20, up to about 1:30, up to about 1:40, up to about 1:50, up to about 1:60, up to about 1:70, up to about 1:80, up to about 1:90, up to about 1:100 or more.

Methods of Analysis Involving a Fluorescence Trigger

Blood cells emit different magnitudes of fluorescence signals upon excitation of the fluorescent dye by a source of light. The differences in magnitude of fluorescence signals arise in part from the quantity of nucleic acids, namely DNA, inside the cells. The greater the quantity of DNA, the greater the likelihood of higher fluorescence signals. Differences in magnitude of fluorescence also arise from, e.g., the ability of a fluorescent dye to penetrate cell membranes, the size of the fluorescent dye molecules, the binding kinetics between the fluorescent dye and the bound nucleic acid, the binding affinity between the fluorescent dye and the nucleic acid, and other such factors.

Mature RBCs emit minimal fluorescence signals because there is no DNA within mature RBCs. Nucleated red blood cells (nRBCs) emit very strong fluorescence signals, because not only is DNA present inside the nuclei of the nRBCs, but also the staining occurs more readily because the membranes of the nRBCs are destroyed during the lysis procedure. Unlysed RBCs or RBC fragments do not emit fluorescence, although in some cases they may emit very weak auto-fluorescence.

As such, the systems and methods presented herein use a fluorescence trigger in combination with WBC analysis reagents to analyze WBCs within a sample. For example, a fluorescence trigger, usually set between signals from RBCs and signals from WBCs, can be used to collect signals from WBCs separately for further analysis. In other words, the use of a fluorescence trigger allows signals from RBCs to be separated out, or removed from the analysis, which facilitates more accurate measurement and analysis of WBCs and WBC sub-populations in the sample by eliminating the interference from RBC signals. Examples of using an FL1, or fluorescence trigger are shown in FIGS. 1-5. FIG. 1 is a scattergram of FL1 vs. IAS that demonstrates the use of a fluorescent trigger for eliminating any fragments of RBCs (nuclei-free particles) and collecting only nuclei-containing events (e.g., WBCs and/or nRBCs). In FIG. 1, the fluorescent dye in the WBC analysis reagent was acridine orange, and the concentration of the fluorescent dye was 3.8 μM. Use of a WBC analysis reagent containing acridine orange as the fluorescent dye (even with drastically different concentrations of the dye, i.e., 11.3 μM down to 0.022 μM as shown in FIG. 6) and a properly set FL1 trigger facilitates identification of nuclei-containing events by establishing a threshold level on FL1. Consequently, only the events above the FL1 trigger (e.g., WBCs and/or nRBCs, if present) are captured for further analysis.

Use of Optical and Fluorescence Channels for Analysis

Aspects of the invention involve the use of optical and fluorescence channels for analyzing WBCs in a blood sample. For example, in some embodiments, a WBC differential analysis is conducted by means of Multiple Angle Polarized Scattering Separation technology (MAPSS), with enhancement from fluorescence information. At least one photodiode, or at least one photomultiplier tube, or both at least one photodiode and at least one photomultiplier tube, are needed to detect light scattered by each blood cell passing through a flow cell. Two or more photodiodes are used for measuring ALL signals, which measure about 0° scatter, and IAS signals, which measure low angle (e.g., about 3° to about 15°) scatters. Two or more photomultiplier tubes (or avalanche photodiodes) are used for detecting large angle (e.g., 90°) PSS signals and large angle (e.g., 90°) DSS signals. Additional photomultiplier tubes are needed for FL1 measurements within appropriate wavelength range(s), depending on the choice of wavelength of the source of light. Each event captured on the system thus exhibits a plurality of dimensions of information, such as ALL, IAS (one or more channels), PSS, DSS, and fluorescence (one or more channels). The information from these detection channels is used for further analysis of blood cells.

Figure 14:
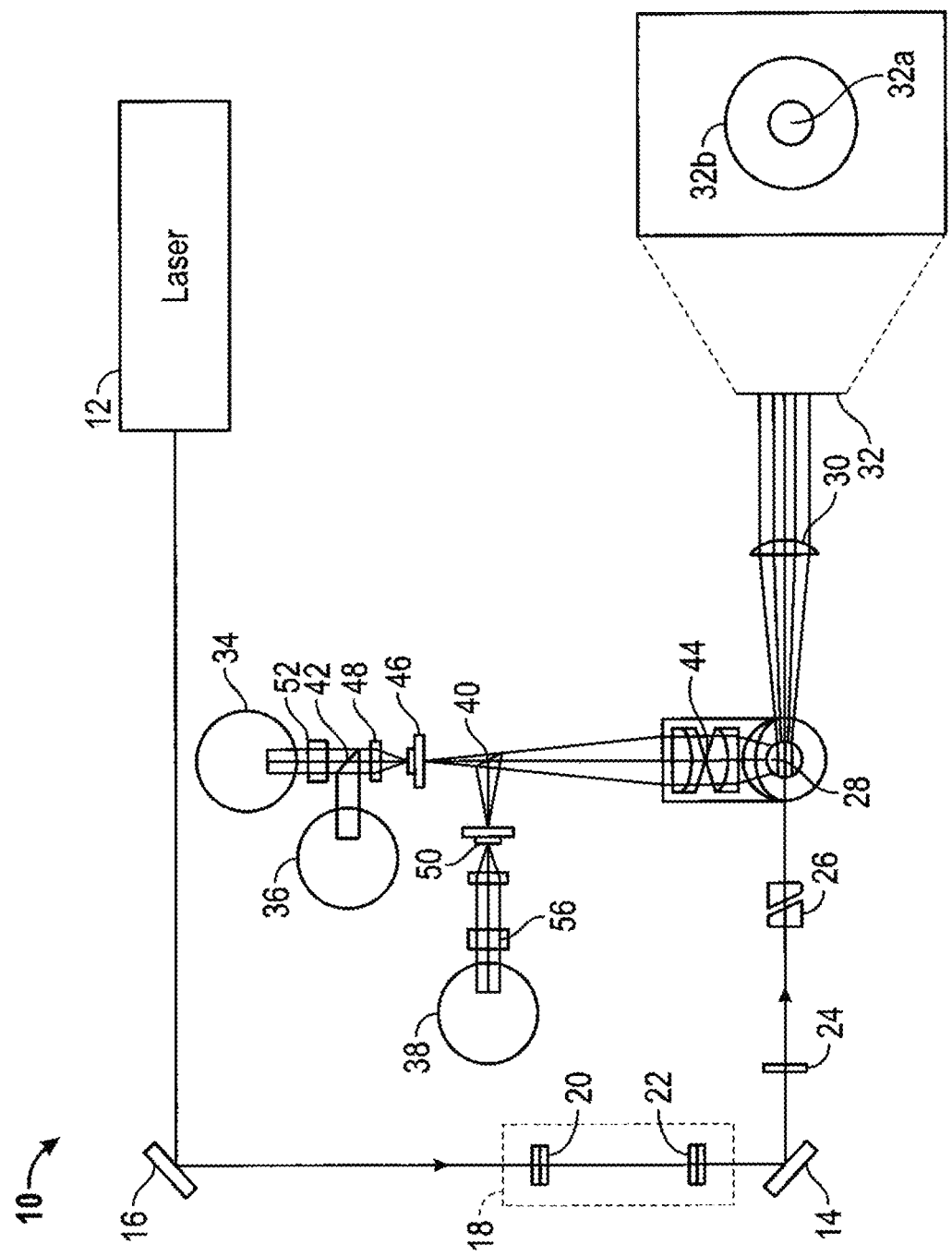
FIG. 14 is a schematic diagram illustrating the illumination and detection optics of an apparatus suitable for hematology analysis (including flow cytometry).

FIG. 14 is a schematic diagram illustrating the illumination and detection optics of an apparatus suitable for hematology analysis (including flow cytometry). Referring now to FIG. 14, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter. The apparatus depicted in FIG. 14 is merely an example of an apparatus that may be used to carry out the methods described herein.

In the discussion that follows, the source of light is preferably a laser. However, other sources of light can be used, such as, for example, lamps (e.g., mercury, xenon). The source of light can be a vertically polarized air-cooled Coherent Cube laser, commercially available from Coherent, Inc., Santa Clara, Calif. In some embodiments, lasers having wavelengths ranging from 350 nm to 700 nm can be used. Operating conditions for the laser are substantially similar to those of lasers currently used with "CELL-DYN" automated hematology analyzers.

Additional details relating to the flow cell, the lenses, the focusing lens, the fine-beam adjust mechanism and the laser focusing lens of a suitable automated hematology analyzer can be found, e.g., in U.S. Pat. No. 5,631,165, incorporated herein by reference in its entirety, particularly at column 41, line 32 through column 43, line 11. The forward optical path system shown in FIG. 14 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS). The second photomultiplier tube 36 (PMT2) measures polarized side scatter (PSS), and the third photomultiplier tube 38 (PMT3) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 14, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include band-pass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

While select portions of U.S. Pat. No. 5,631,165 are referenced above, U.S. Pat. No. 5,631,165 is incorporated herein by reference in its entirety.

In addition to the information collected from the four traditional MAPSS channels (ALL, IAS, PSS, DSS), the FL1 channel further distinguishes the cell sub-populations from one another. The combined quantitative information from all optical dimensions and the fluorescence dimension provides an enhanced, and more reliable, differential analysis for samples of blood containing WBCs.

The methods described herein enhance WBC analysis for hematology analyzers and provide a more accurate WBC count and a more accurate classification of WBC sub-populations, because the interference from unlysed RBCs and RBC fragments is substantially eliminated. The use of fluorescence provides further information to improve differential analysis of WBCs. The methods described herein show advantages over traditional methods when analyzing samples having rstRBCs and samples having fragile WBCs.

Example WBC Analysis Reagent Formulations

Various examples of WBC analysis reagent formulations are provided below. The formulations provided below merely serve as examples, and are in no way limiting. Any of a variety of combinations of the components described herein can be utilized in WBC analysis reagents in accordance with embodiments of the invention.

Example Formulation 1

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Formaldehyde | 0.220% |
| Acridine Orange | 3.8 µM |

Example Formulation 2

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Formaldehyde | 0.220% |
| Hexidium Iodide | 1.3 µM |

Example Formulation 3

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Formaldehyde | 0.220% |
| SYTORNA Select | 1.3 µM |

Example Formulation 4

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Formaldehyde | 0.220% |
| SYTO 12 | 1.3 µM |

Example Formulation 5

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Formaldehyde | 0.220% |
| SYTO 14 | 1.3 µM |

Example Formulation 6

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Glutaraldehyde | 0.200% |
| Acridine Orange | 0.0003% |

Example Formulation 7

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Butoxyethanol | 0.500% |
| Acridine Orange | 0.0003% |

Example Formulation 8

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Phenoxyethanol | 0.500% |
| Acridine Orange | 0.0003% |

Example Formulation 9

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | 0.250% |
| Isopropyl Alcohol | 0.500% |
| Acridine Orange | 0.0003% |

Example Formulation 10

| Component | Concentration |
|---|---|
| Sodium Acetate | 0.152% |
| Sodium Bicarbonate | 0.203% |
| Saponin | 0.014% |
| Proclin 300 | 0.060% |
| Ammonium Chloride | Varied, 0.125%-0.5% |
| Formaldehyde | 0.220% |
| Acridine Orange | 0.0003% |

Example Formulation 11

| Component | A | B | C | D | E |
|---|---|---|---|---|---|
| Sodium Acetate | 0.152% | 0.152% | 0.152% | 0.152% | 0.152% |
| Sodium Bicarbonate | 0.203% | 0.203% | 0.203% | 0.203% | 0.203% |
| Saponin | 0.014% | 0.014% | 0.014% | 0.014% | 0.014% |
| Proclin 300 | 0.060% | 0.060% | 0.060% | 0.060% | 0.060% |
| Ammonium Chloride | 0.125% | 0.125% | 0.125% | 0.125% | 0.125% |
| Sodium Chloride | No | 0.033% | 0.066% | 0.100% | 0.133% |
| Formaldehyde | 0.220% | 0.220% | 0.220% | 0.220% | 0.220% |
| Acridine Orange | 0.0003% | 0.0003% | 0.0003% | 0.0003% | 0.0003% |
| Osmolality (mOsm) | 149 | 158 | 168 | 181 | 191 |

EXAMPLES

FIGS. 1-5 show WBC differential scattergrams (FL1 vs. IAS) for a normal whole blood specimen that was analyzed using the WBC analysis reagents and systems described above in Example Formulations 1-5, respectively. As can be seen in FIGS. 1-5, the WBC analysis reagents were able to sufficiently distinguish and differentiate the WBCs in the samples.

FIGS. 6A-6D show WBC differential scattergrams (PSS vs. ALL and FL1 vs. IAS) for four different WBC analysis reagent formulations. The results indicate that similar WBC differentials are obtained even when the concentrations of membrane-permeable fluorescent dye in the WBC analysis reagent varied significantly. The four formulations tested were similar to those in Example Formulation 1, except the concentrations of acridine orange were prepared at 11.3 µM (1×), 1.13 µM (0.1×), 0.11 µM (0.01×), and 0.022 µM (0.002×), with the voltages of FL1 PMT set at 375 V, 420 V, 475 V and 520 V, respectively.

Figure 7A:
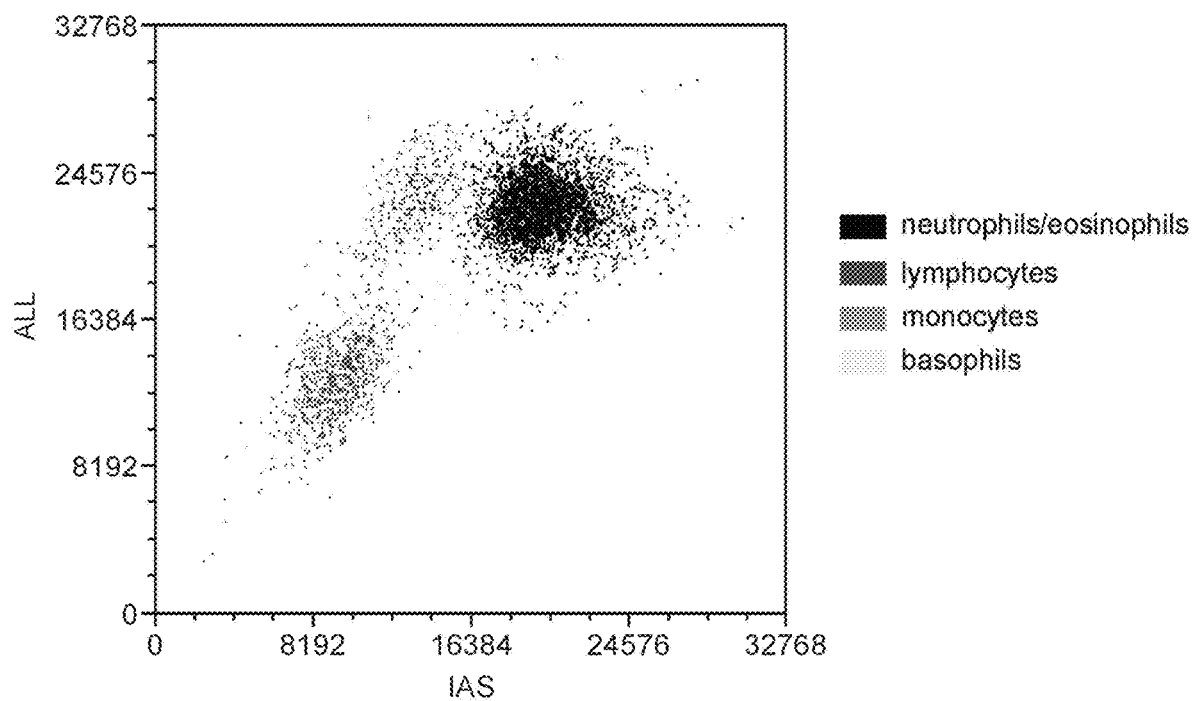
FIG. 7A shows two WBC scattergrams (ALL vs. IAS and FL1 vs. ALL) obtained using a WBC analysis reagent containing 0.22% formaldehyde (same formulation as example WBC analysis reagent #1). Neutrophils/eosinophils, lymphocytes, monocytes, and basophils are shown in the scattergrams.
Figure 7A:
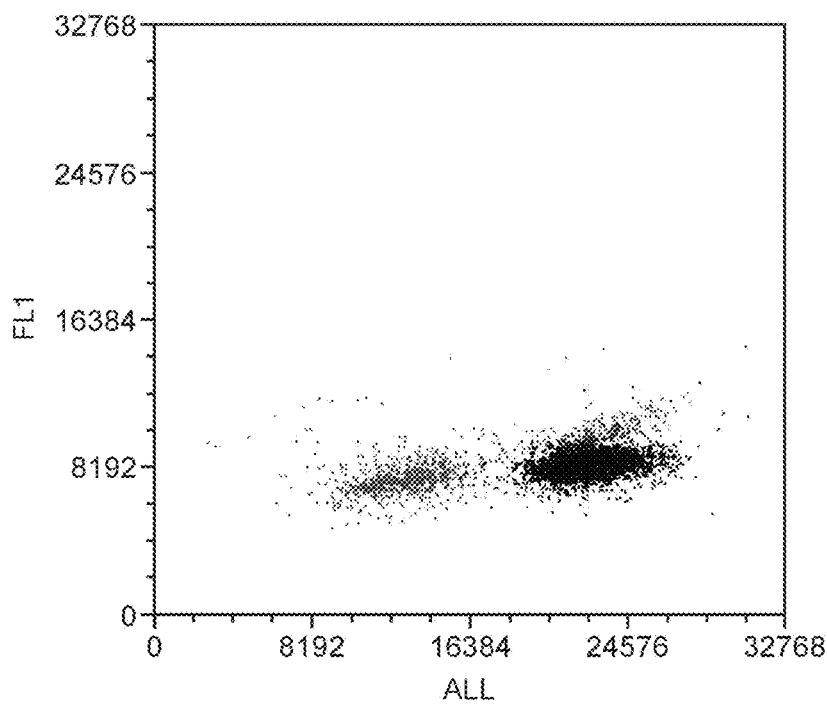
Figure 7B:
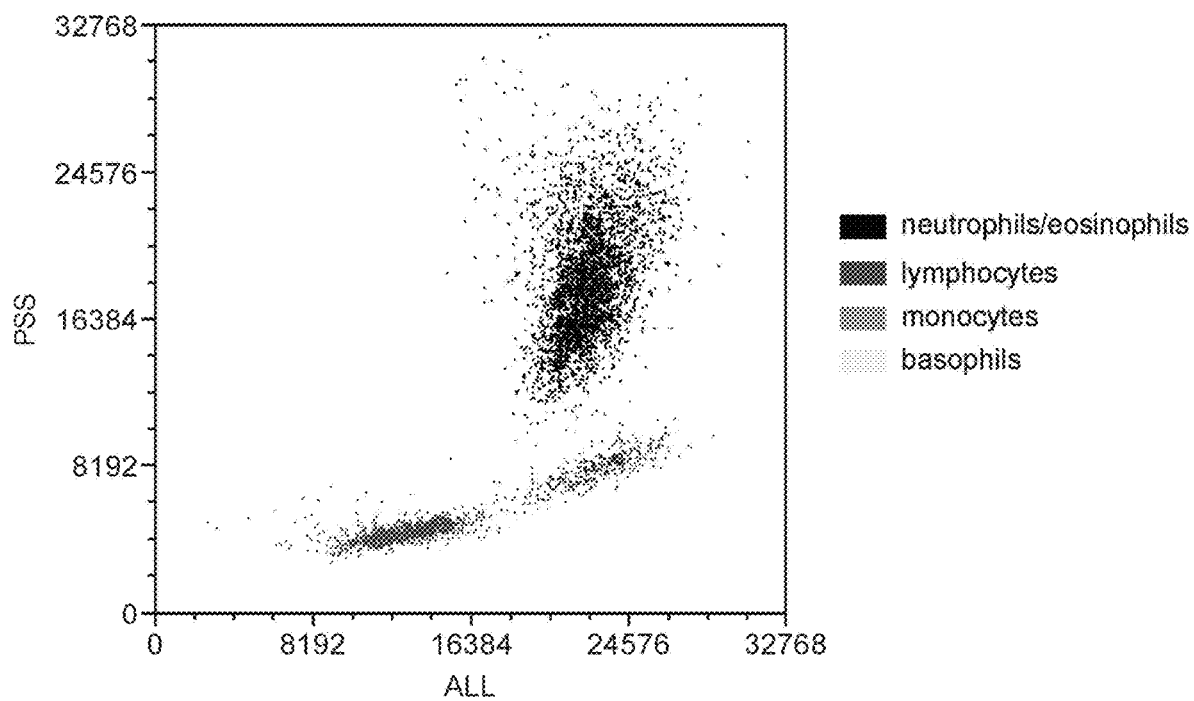
FIG. 7B shows two WBC scattergrams (PSS vs. ALL and FL1 vs. IAS) obtained using a WBC analysis reagent containing 0.22% formaldehyde (same formulation as example WBC analysis reagent #1). Neutrophils/eosinophils, lymphocytes, monocytes, and basophils are shown in the scattergrams.
Figure 7B:
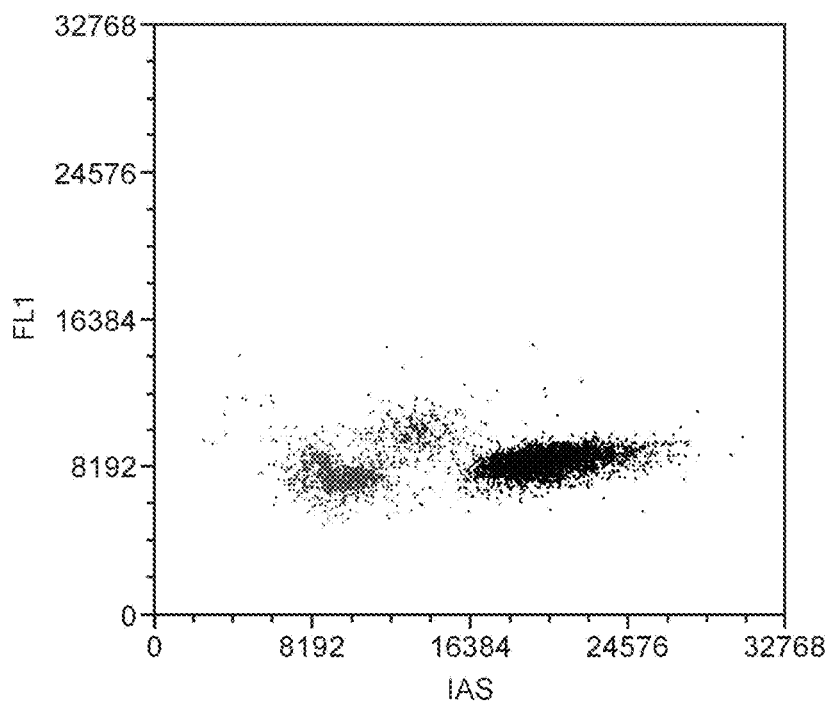
Figure 7C:
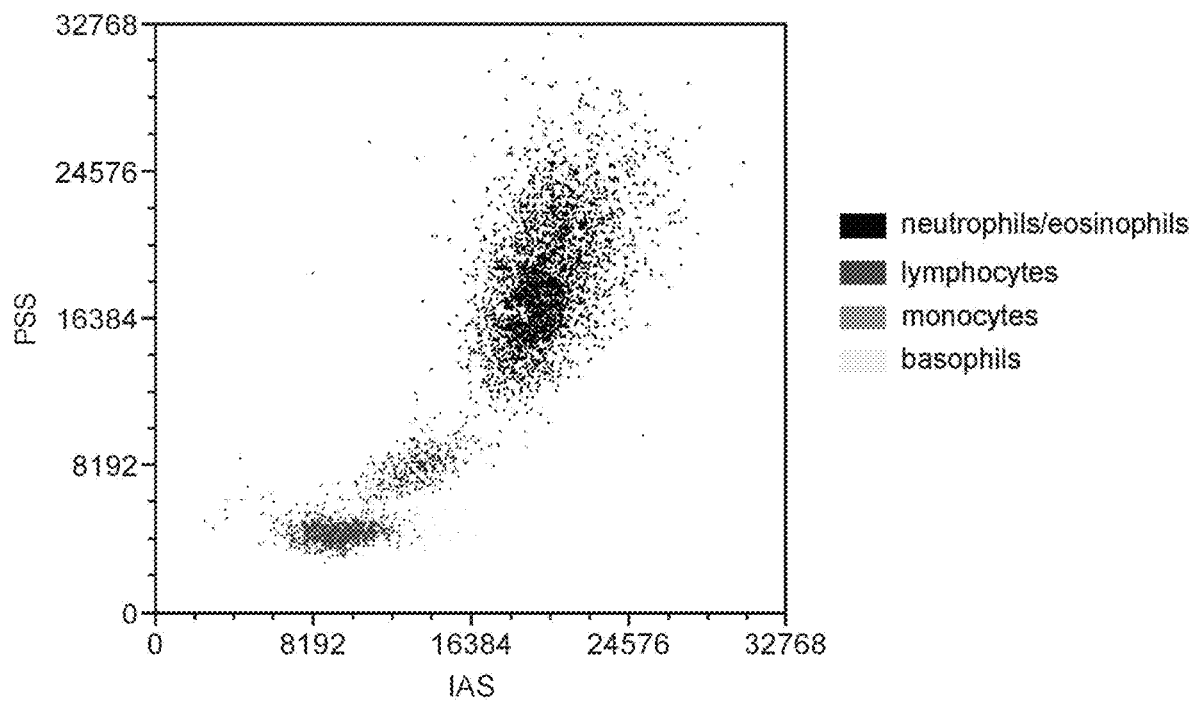
FIG. 7C shows two WBC scattergrams (PSS vs. IAS and FL1 vs. PSS) obtained using a WBC analysis reagent containing 0.22% formaldehyde (same formulation as example WBC analysis reagent #1). Neutrophils/eosinophils, lymphocytes, monocytes, and basophils are shown in the scattergrams.
Figure 7C:
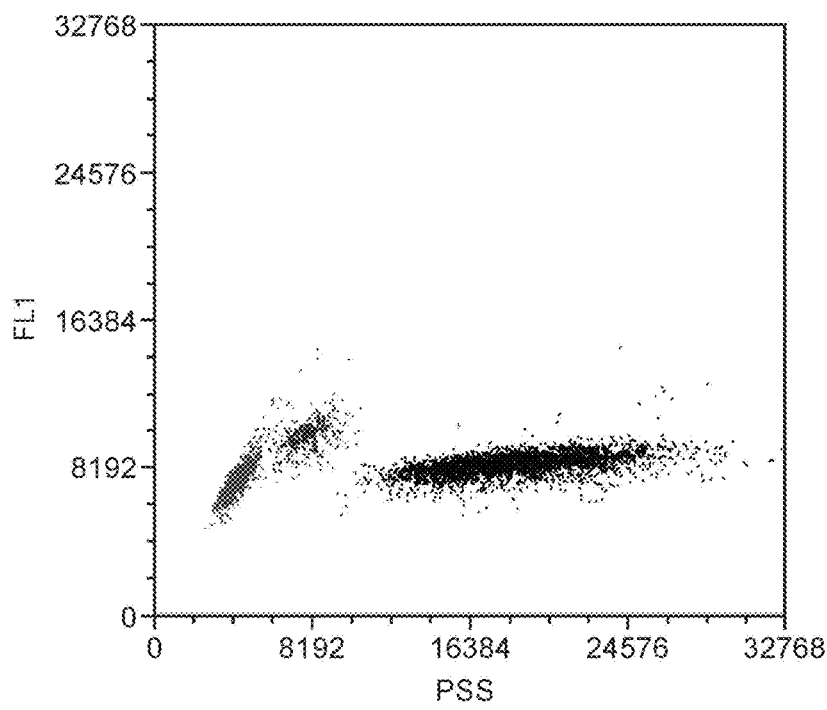

FIGS. 7A-7C show various WBC scattergrams of a normal whole blood specimen that was analyzed using a WBC analysis reagent containing 0.22% formaldehyde as the WBC protecting agent (same formulation as Example Formulation 1).

Figure 8A:
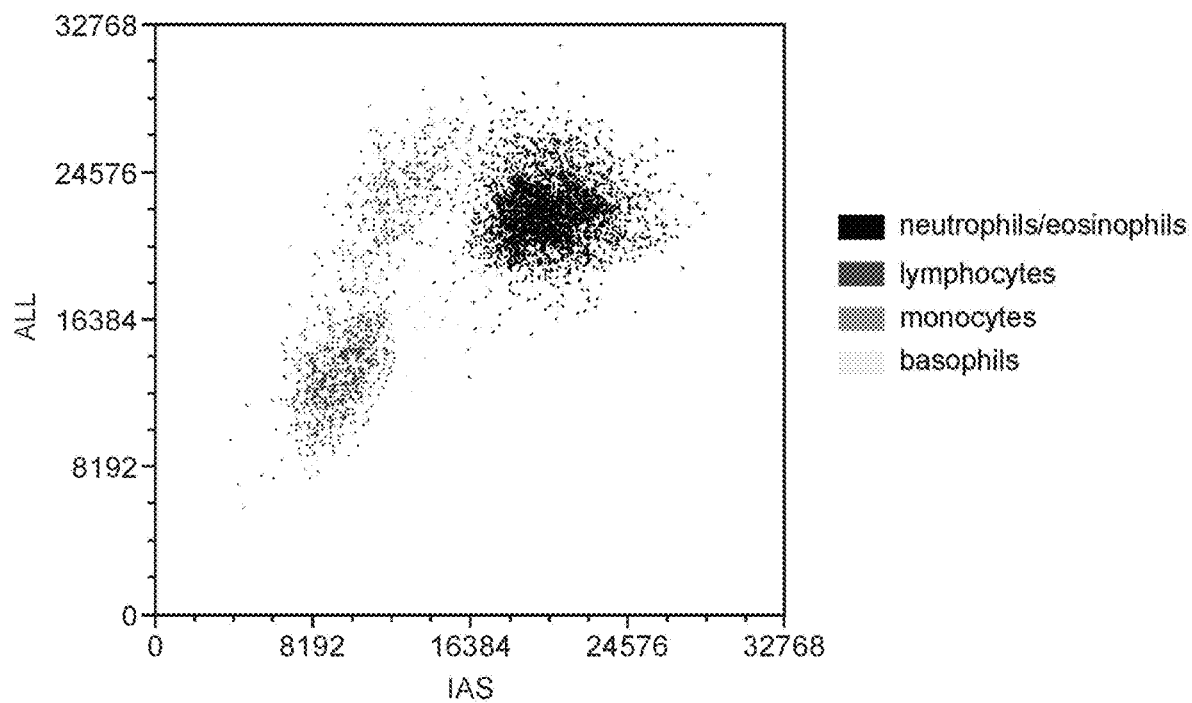
FIG. 8A shows two WBC scattergrams (ALL vs. IAS and FL1 vs. ALL) obtained using a WBC analysis reagent containing 0.2% glutaraldehyde (same formulation as example WBC analysis reagent #6). Neutrophils/eosinophils, lymphocytes, monocytes, and basophils are shown in the scattergrams.
Figure 8A:
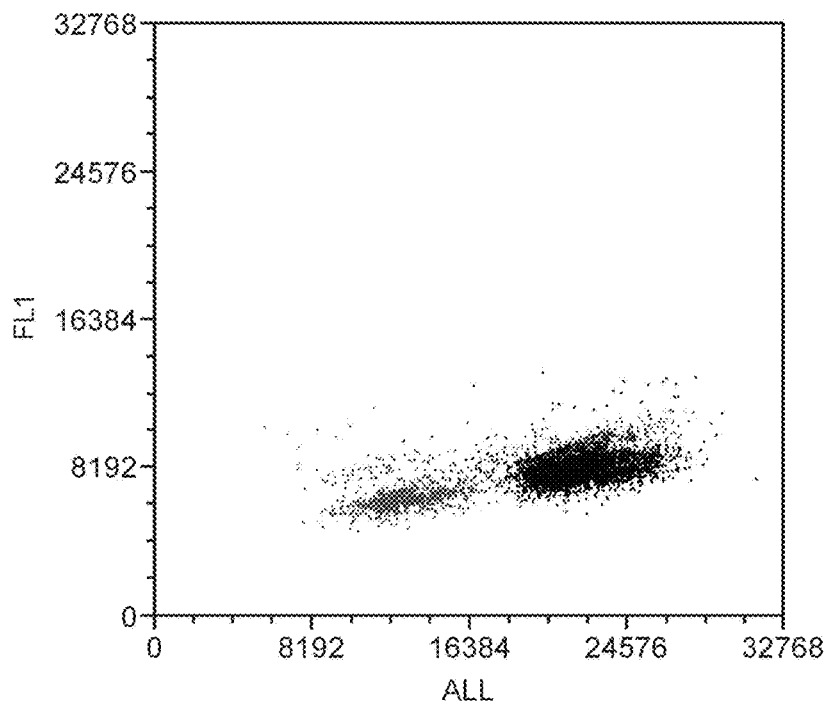
Figure 8B:
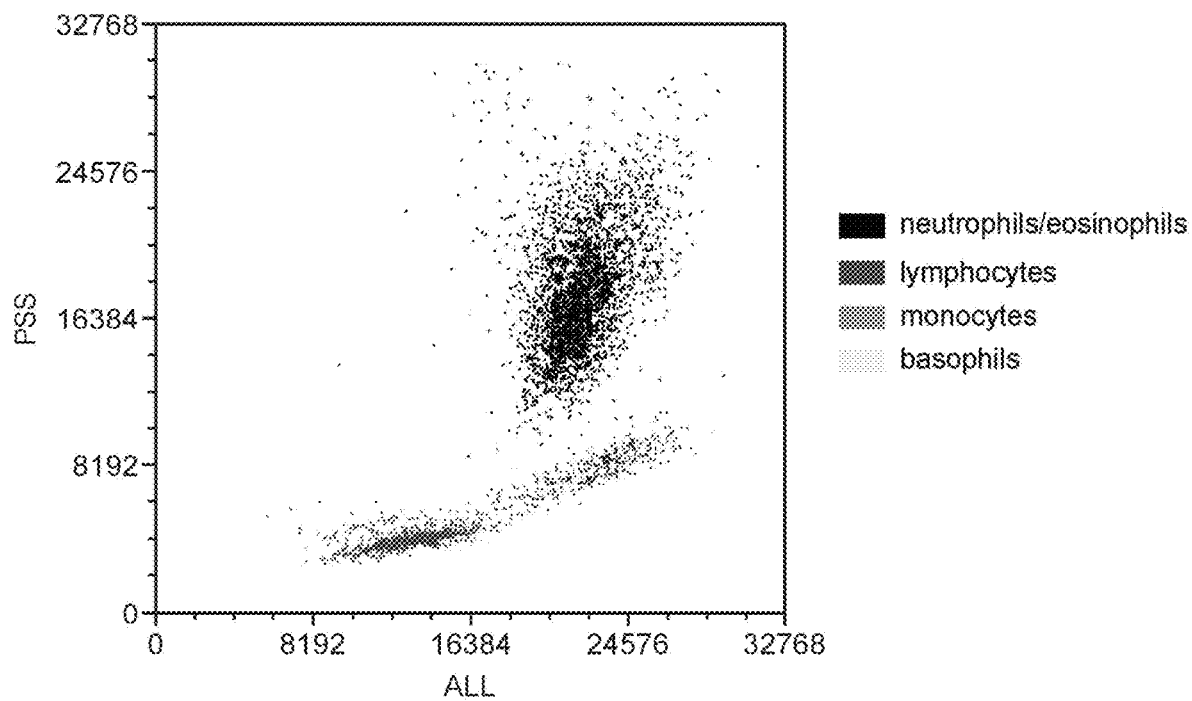
FIG. 8B shows two WBC scattergrams (PSS vs. ALL and FL1 vs. IAS) obtained using a WBC analysis reagent containing 0.2% glutaraldehyde (same formulation as example WBC analysis reagent #6). Neutrophils/eosinophils, lymphocytes, monocytes, and basophils are shown in the scattergrams.
Figure 8B:
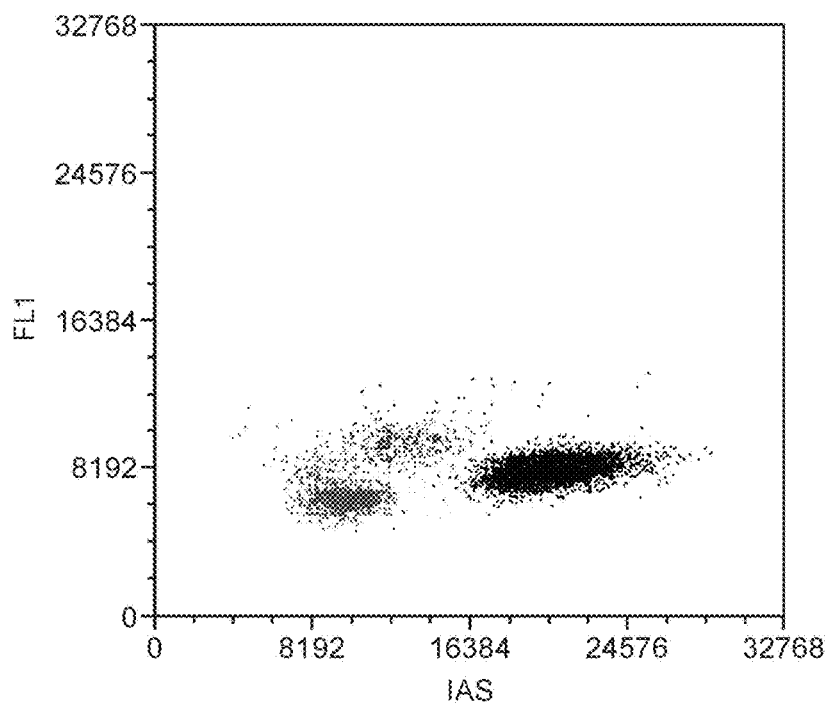
Figure 8C:
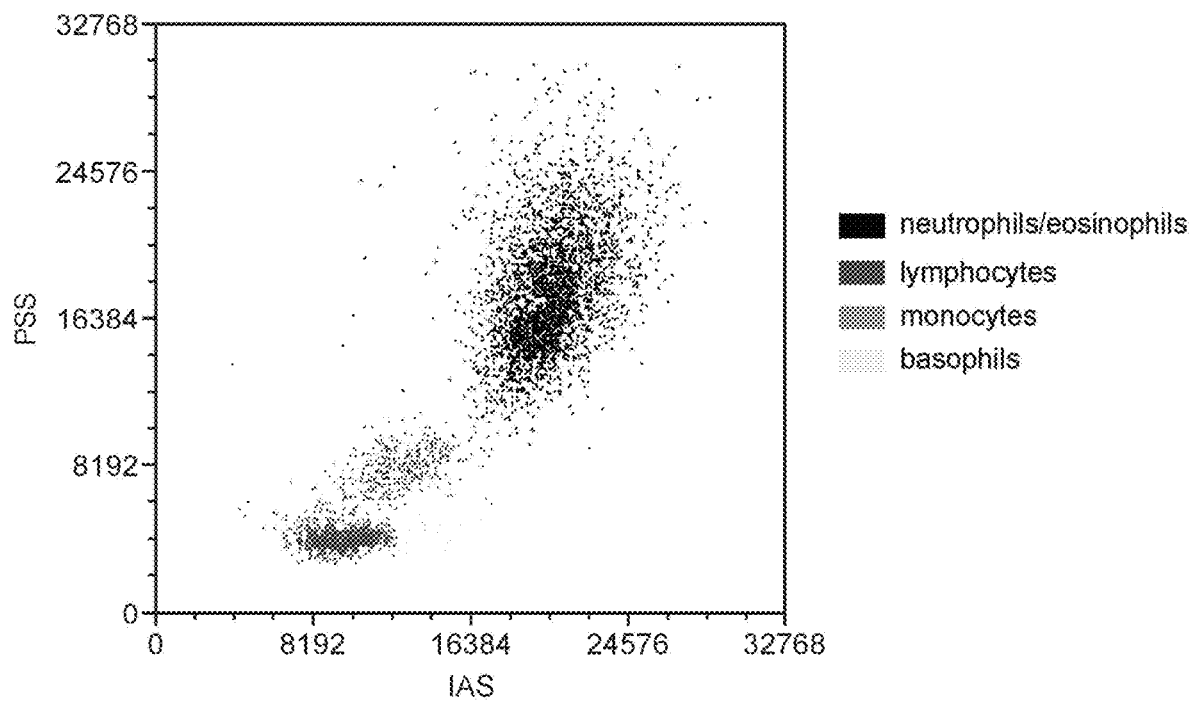
FIG. 8C shows two WBC scattergrams (PSS vs. IAS and FL1 vs. PSS) obtained using a WBC analysis reagent containing 0.2% glutaraldehyde (same formulation as example WBC analysis reagent #6). Neutrophils/eosinophils, lymphocytes, monocytes, and basophils are shown in the scattergrams.
Figure 8C:
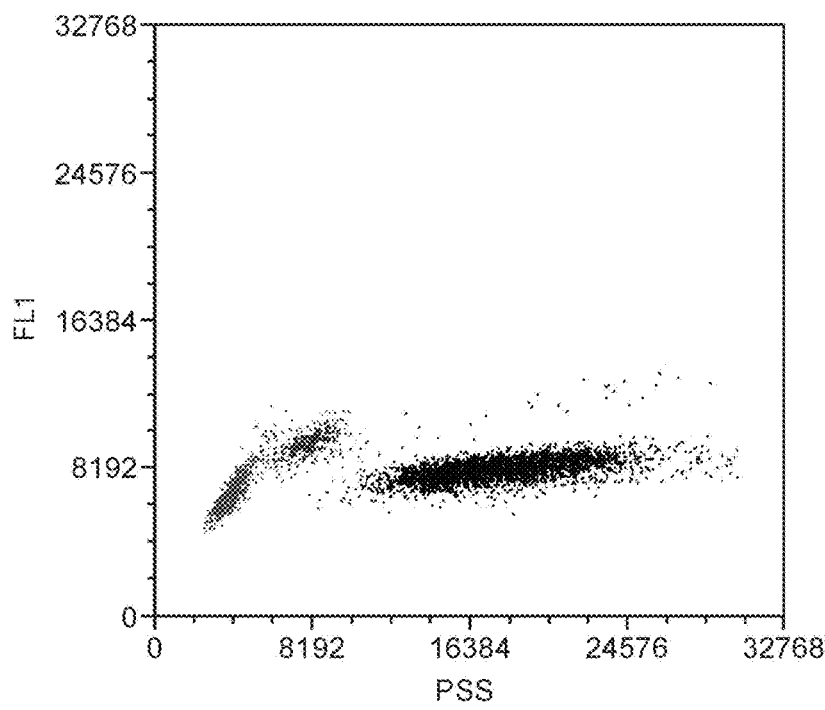

FIGS. 8A-8C show various WBC scattergrams of a normal whole blood specimen that was analyzed using a WBC analysis reagent containing 0.2% glutaraldehyde as the WBC protecting agent (same formulation as Example Formulation 6).

Figure 9A:
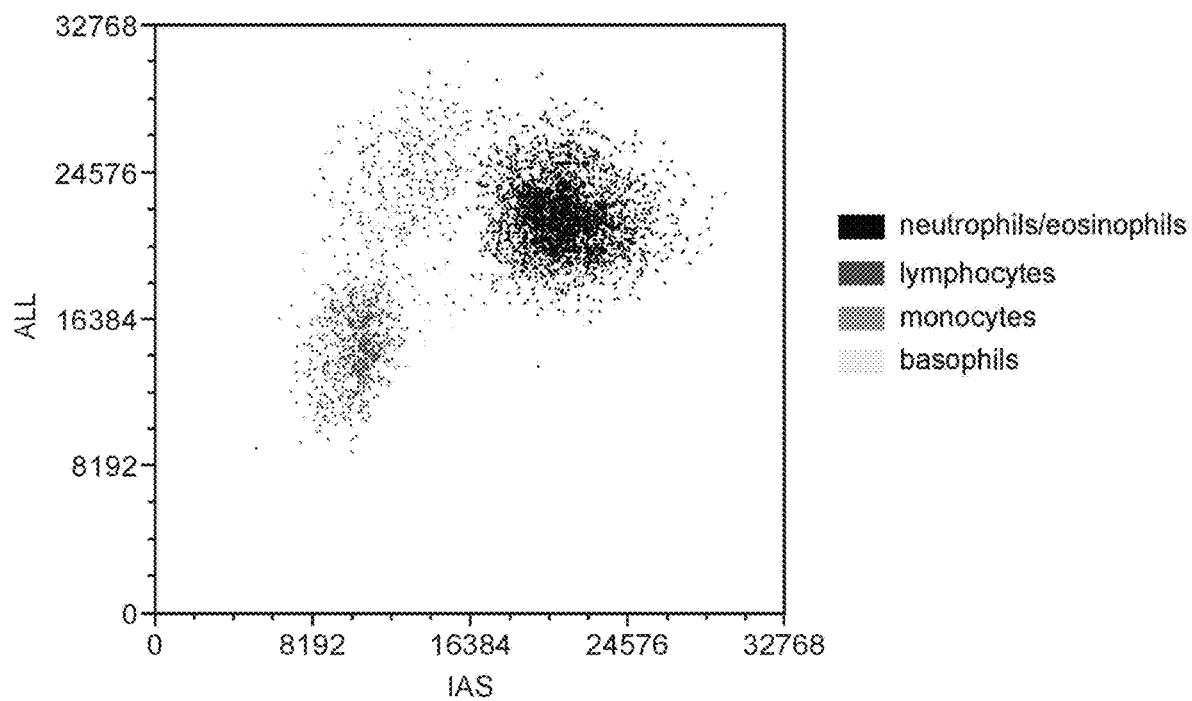
FIG. 9A shows two WBC scattergrams (ALL vs. IAS and FL1 vs. ALL) obtained using a WBC analysis reagent containing 0.5% butoxyethanol (same formulation as example WBC analysis reagent #7). Neutrophils/eosinophils, lymphocytes, monocytes, and basophils are shown in the scattergrams.
Figure 9A:
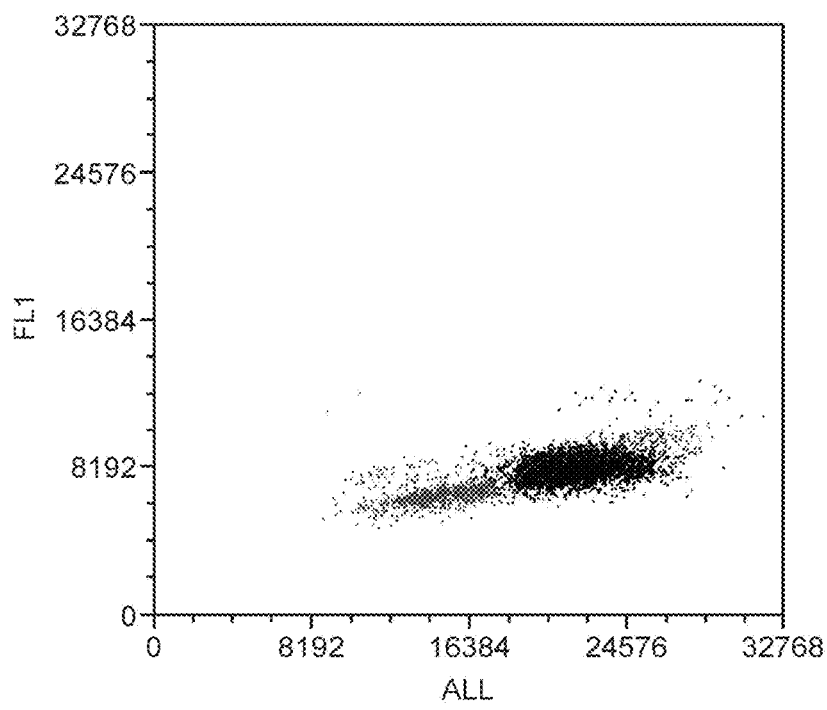
Figure 9B:
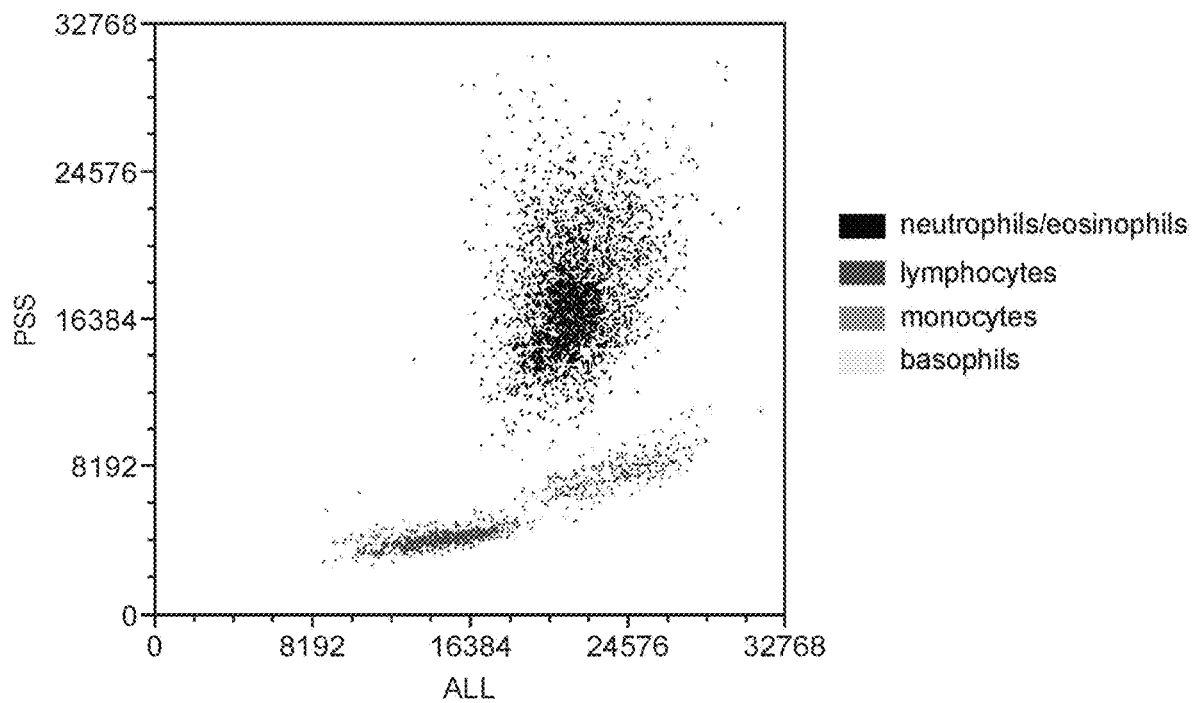
FIG. 9B shows two WBC scattergrams (PSS vs. ALL and FL1 vs. IAS) obtained using a WBC analysis reagent containing 0.5% butoxyethanol (same formulation as example WBC analysis reagent #7). Neutrophils/eosinophils, lymphocytes, monocytes, and basophils are shown in the scattergrams.
Figure 9B:
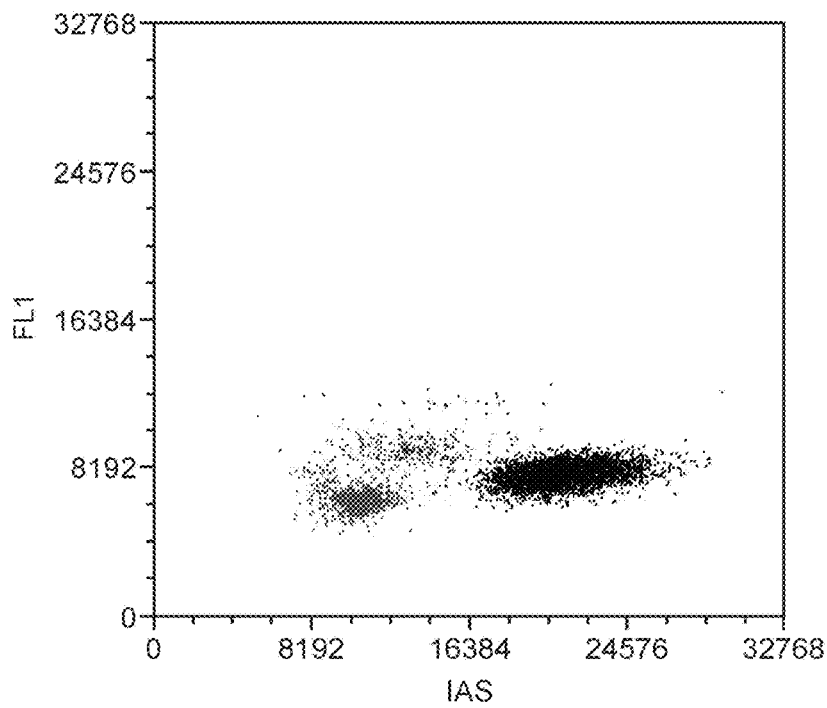
Figure 9C:
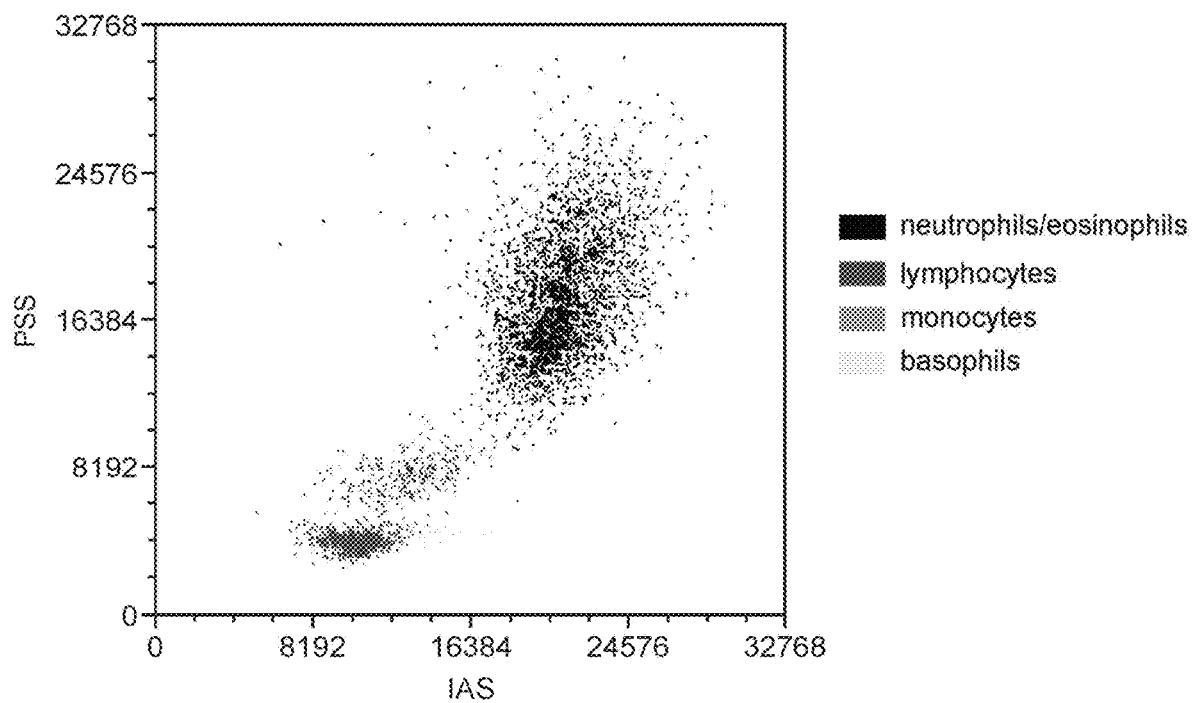
FIG. 9C shows two WBC scattergrams (PSS vs. IAS and FL1 vs. PSS) obtained using a WBC analysis reagent containing 0.5% butoxyethanol (same formulation as example WBC analysis reagent #7). Neutrophils/eosinophils, lymphocytes, monocytes, and basophils are shown in the scattergrams.
Figure 9C:
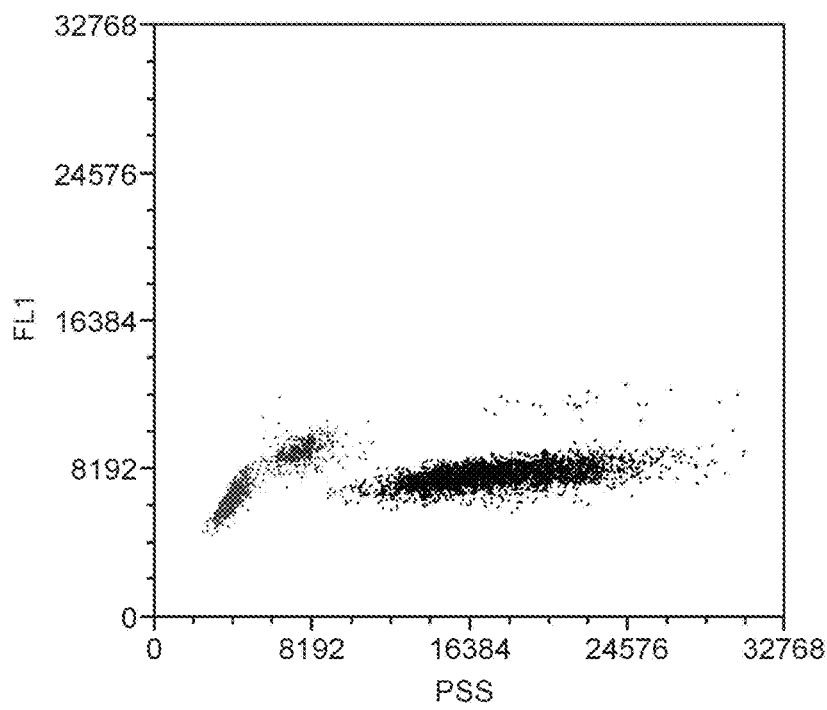

FIGS. 9A-9C show various WBC scattergrams of a normal whole blood specimen that was analyzed using a WBC analysis reagent containing 0.5% butoxyethanol as the WBC protecting agent (same formulation as Example Formulation 7).

Figure 10A:
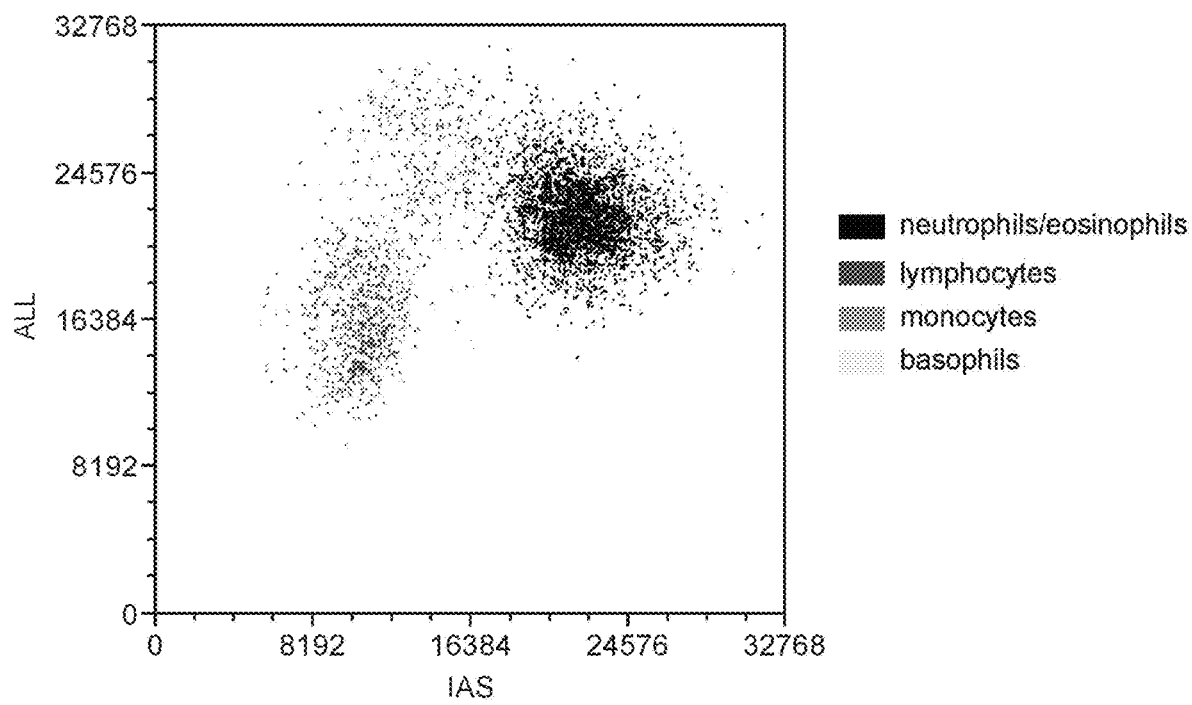
FIG. 10A shows two WBC scattergrams (ALL vs. IAS and FL1 vs. ALL) obtained using a WBC analysis reagent containing 0.5% phenoxyethanol (same formulation as example WBC analysis reagent #8). Neutrophils/eosinophils, lymphocytes, monocytes, and basophils are shown in the scattergrams.
Figure 10A:
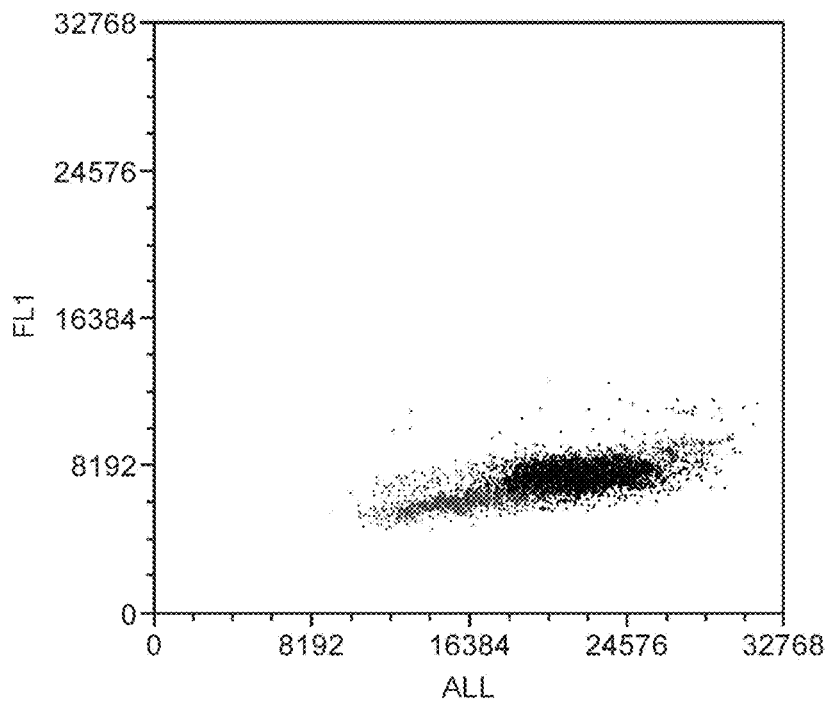
Figure 10B:
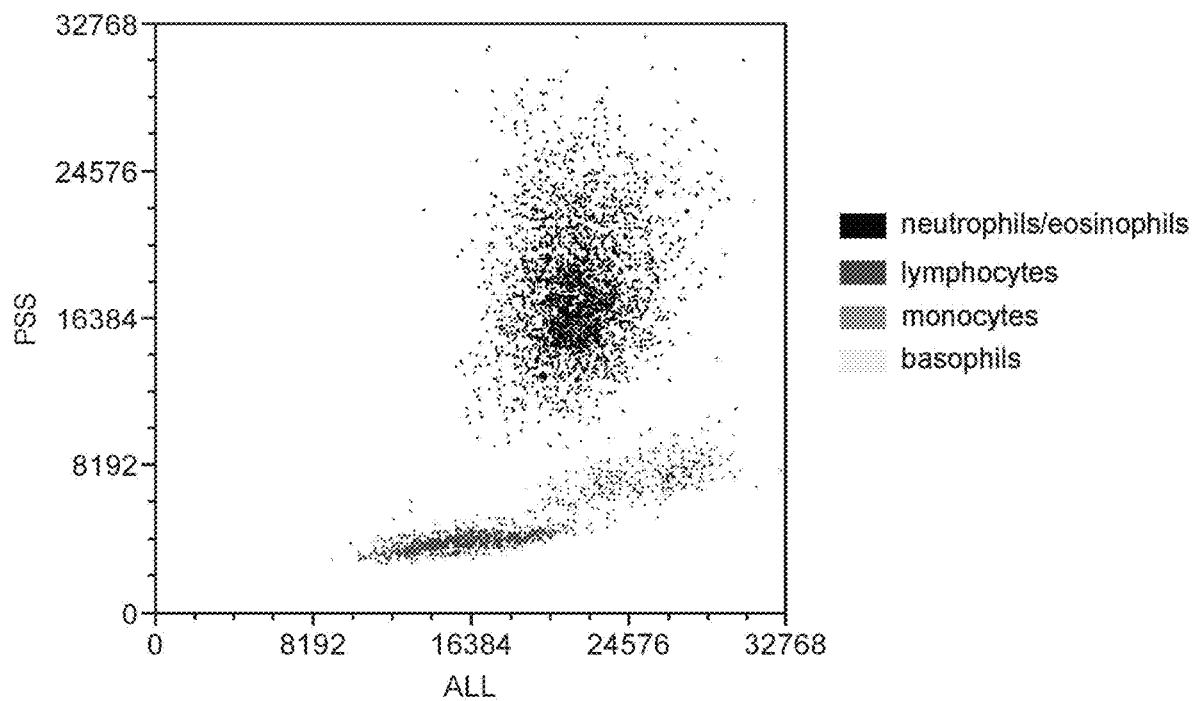
FIG. 10B shows two WBC scattergrams (PSS vs. ALL and FL1 vs. IAS) obtained using a WBC analysis reagent containing 0.5% phenoxyethanol (same formulation as example WBC analysis reagent #8). Neutrophils/eosinophils, lymphocytes, monocytes, and basophils are shown in the scattergrams.
Figure 10B:
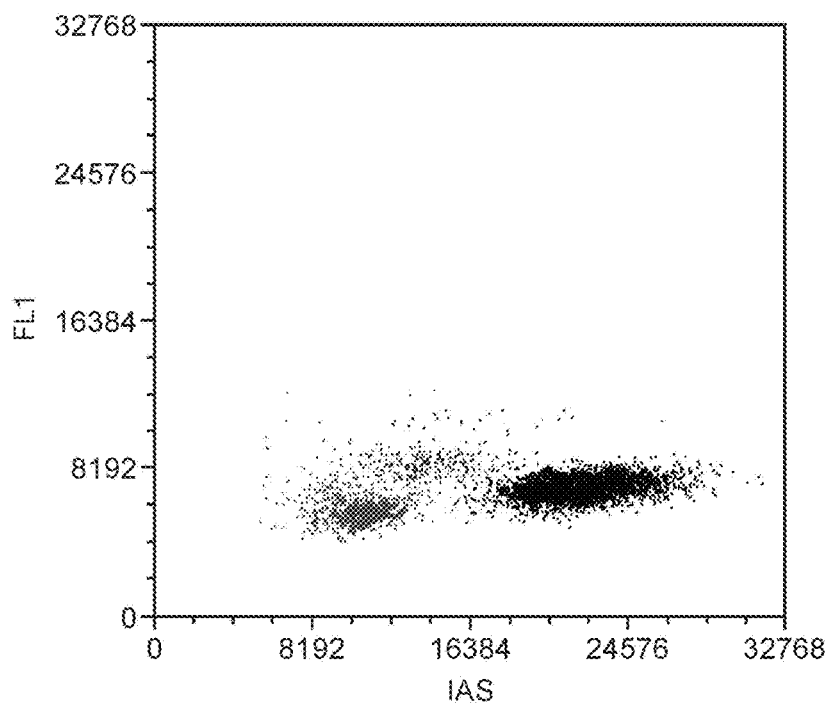
Figure 10C:
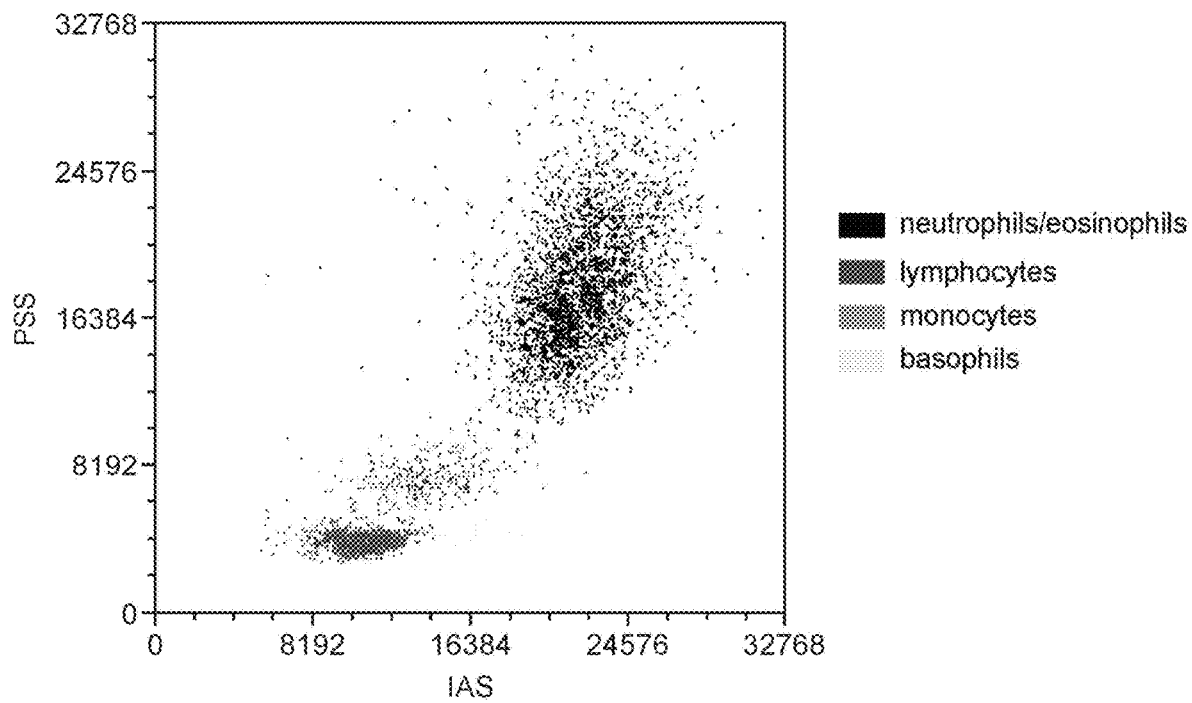
FIG. 10C shows two WBC scattergrams (PSS vs. IAS and FL1 vs. PSS) obtained using a WBC analysis reagent containing 0.5% phenoxyethanol (same formulation as example WBC analysis reagent #8). Neutrophils/eosinophils, lymphocytes, monocytes, and basophils are shown in the scattergrams.
Figure 10C:
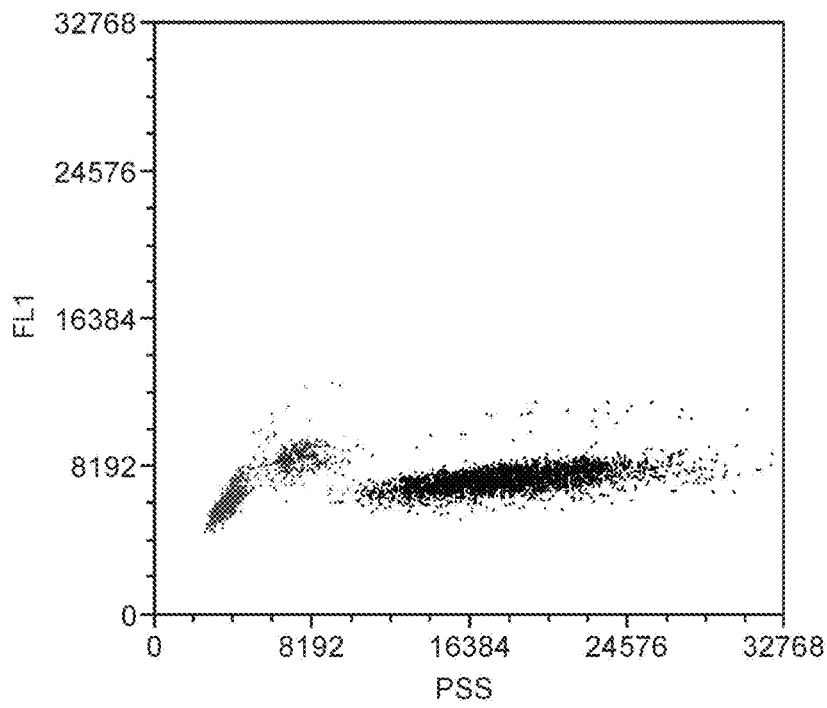

FIGS. 10A-10C show various WBC scattergrams of a normal whole blood specimen that was analyzed using a WBC analysis reagent containing 0.5% phenoxyethanol as the WBC protecting agent (same formulation as Example Formulation 8).

Figure 11A:
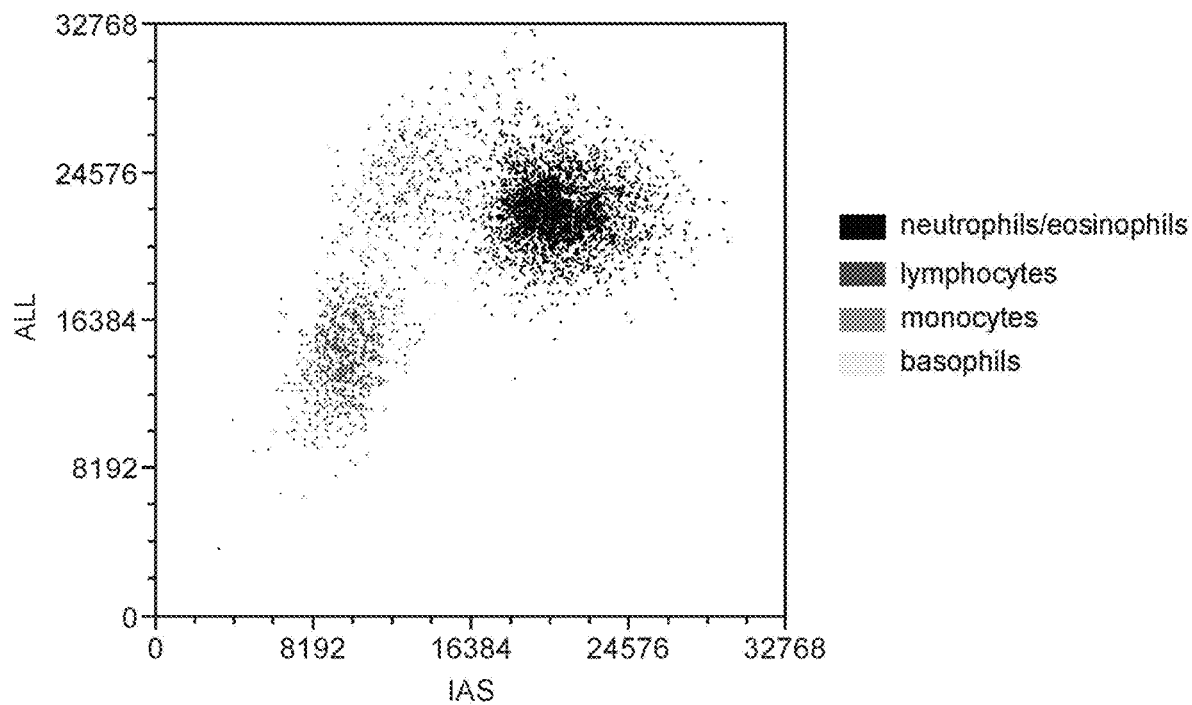
FIG. 11A shows two WBC scattergrams (ALL vs. IAS and FL1 vs. ALL) obtained using a WBC analysis reagent containing 0.5% isopropyl alcohol (same formulation as example WBC analysis reagent #9). Neutrophils/eosinophils, lymphocytes, monocytes, and basophils are shown in the scattergrams.
Figure 11A:
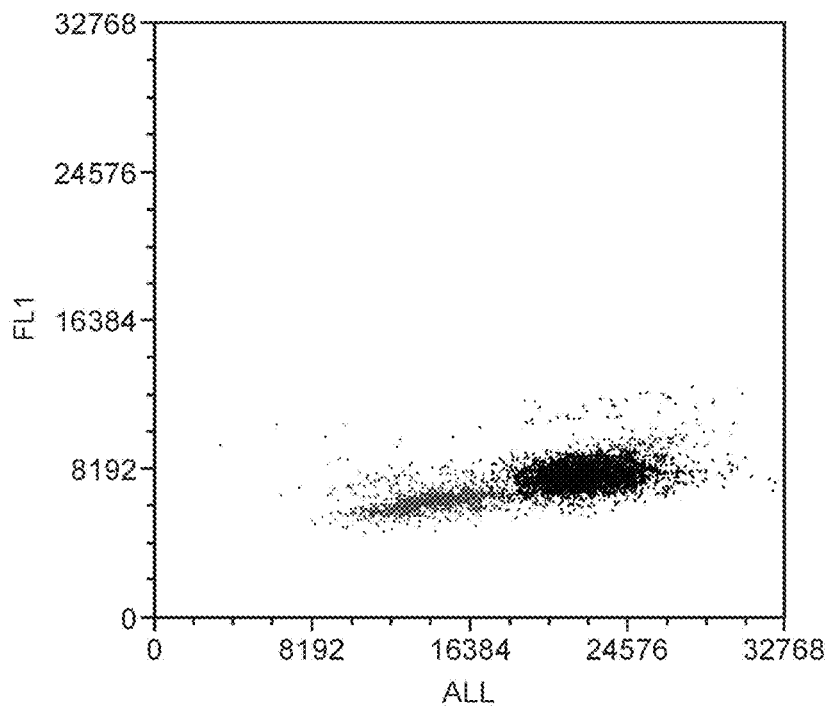
Figure 11B:
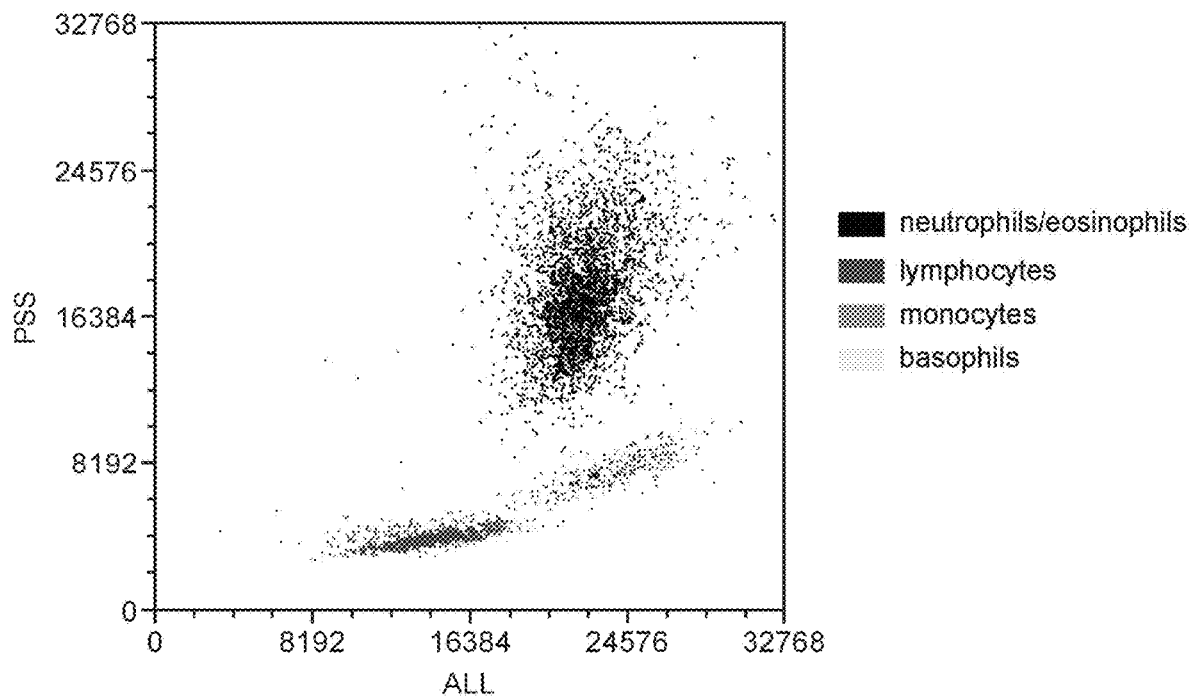
FIG. 11B shows two WBC scattergrams (PSS vs. ALL and FL1 vs. IAS) obtained using a WBC analysis reagent containing 0.5% isopropyl alcohol (same formulation as example WBC analysis reagent #9). Neutrophils/eosinophils, lymphocytes, monocytes, and basophils are shown in the scattergrams.
Figure 11B:
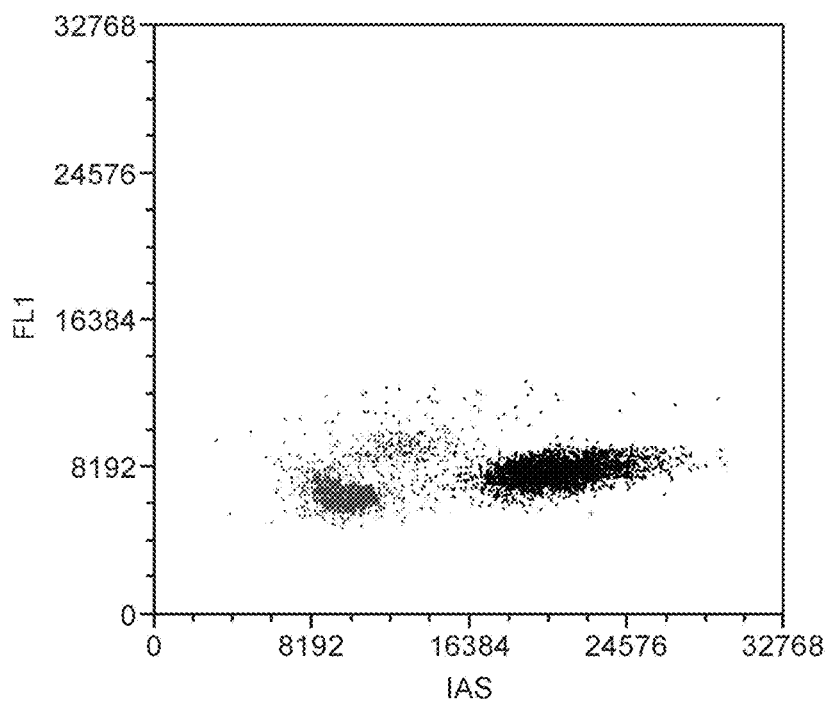
Figure 11C:
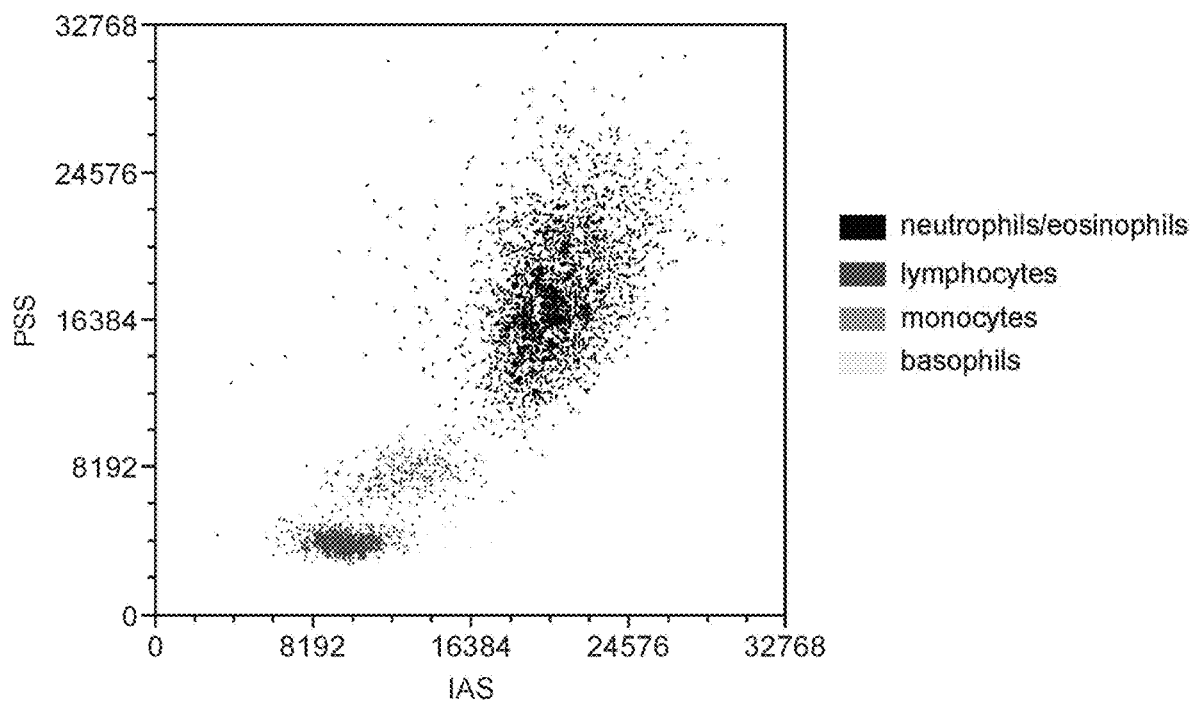
FIG. 11C shows two WBC scattergrams (PSS vs. IAS and FL1 vs. PSS) obtained using a WBC analysis reagent containing 0.5% isopropyl alcohol (same formulation as example WBC analysis reagent #9). Neutrophils/eosinophils, lymphocytes, monocytes, and basophils are shown in the scattergrams.
Figure 11C:
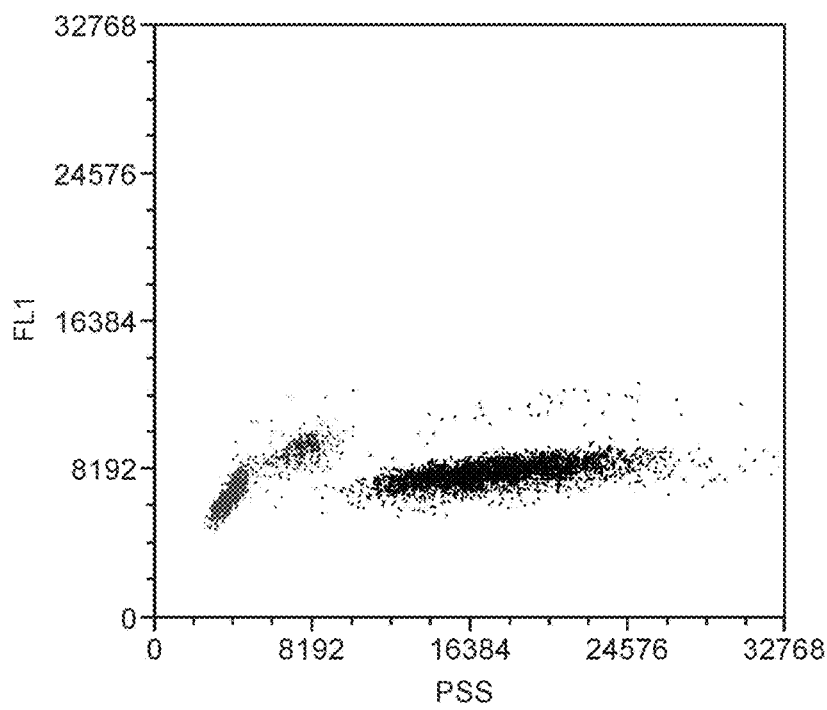
Figure 12A:
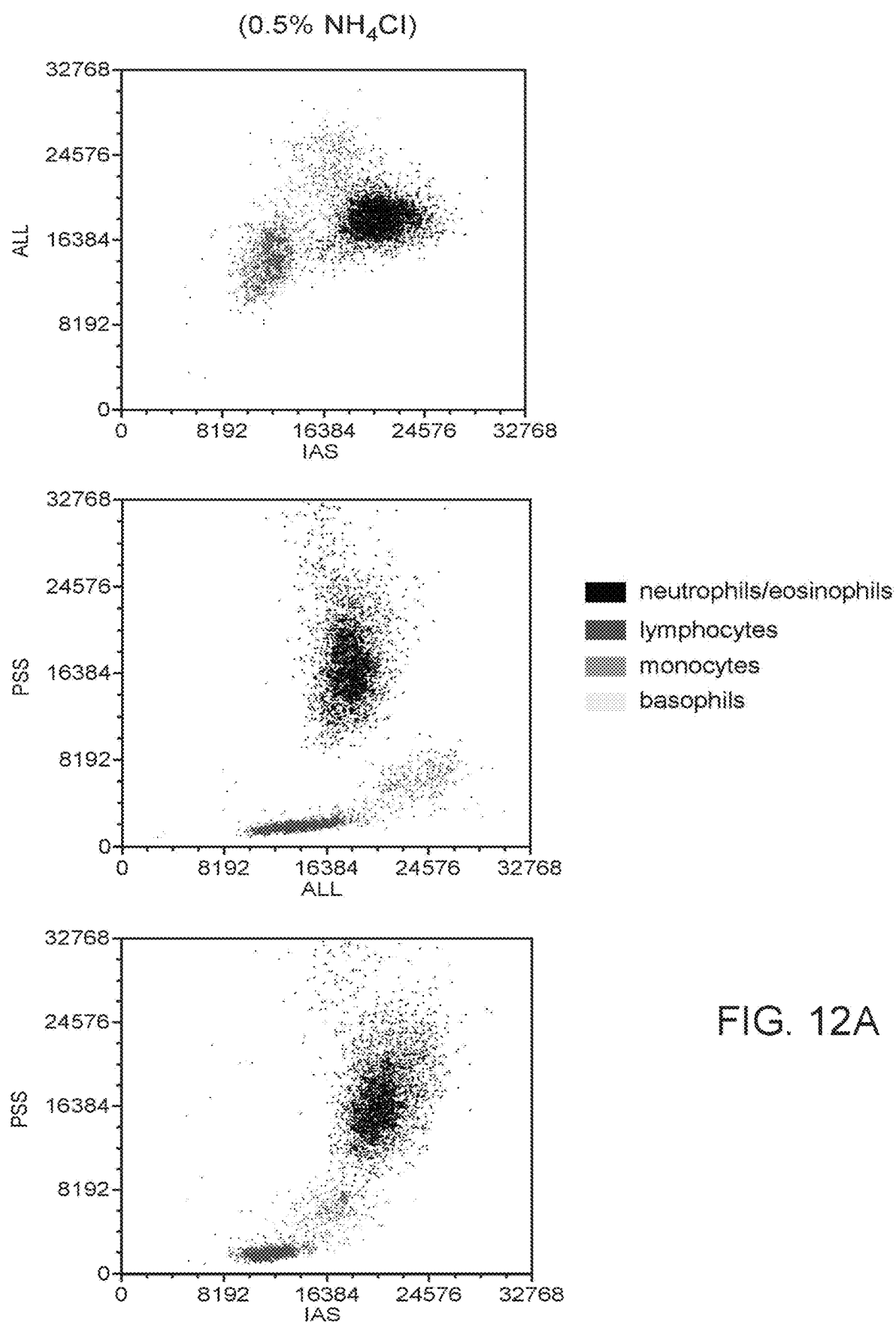
FIG. 12A shows three WBC scattergrams (ALL vs. IAS, PSS vs. ALL, and PSS vs. IAS) obtained using a WBC analysis reagent containing 0.5% ammonium chloride as an osmolality adjustment component. Neutrophils/eosinophils, lymphocytes, monocytes, and basophils are shown in the scattergrams.
Figure 12B:
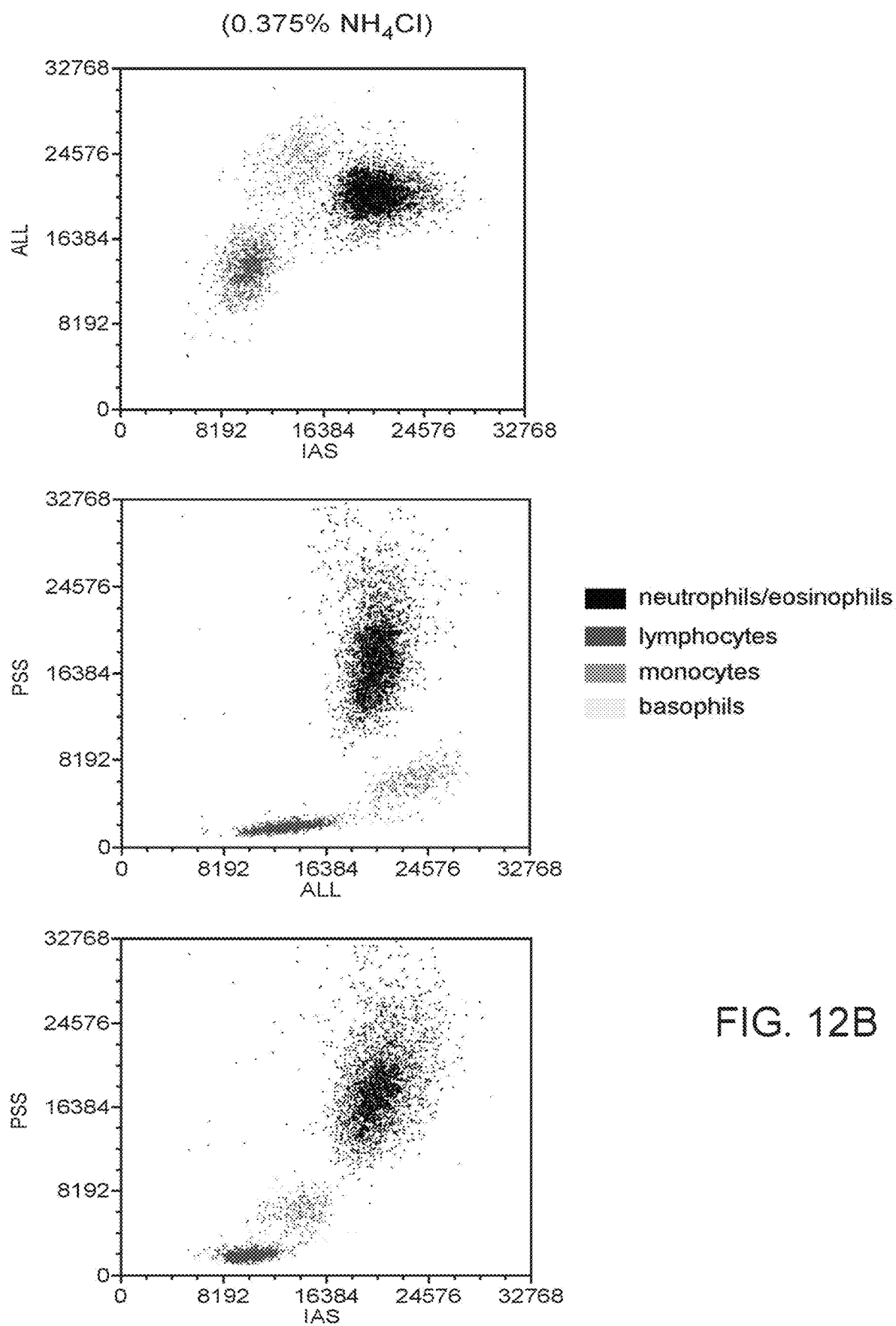
FIG. 12B shows three WBC scattergrams (ALL vs. IAS, PSS vs. ALL, and PSS vs. IAS) obtained using a WBC analysis reagent containing 0.375% ammonium chloride as an osmolality adjustment component. Neutrophils/eosinophils, lymphocytes, monocytes, and basophils are shown in the scattergrams.
Figure 12C:
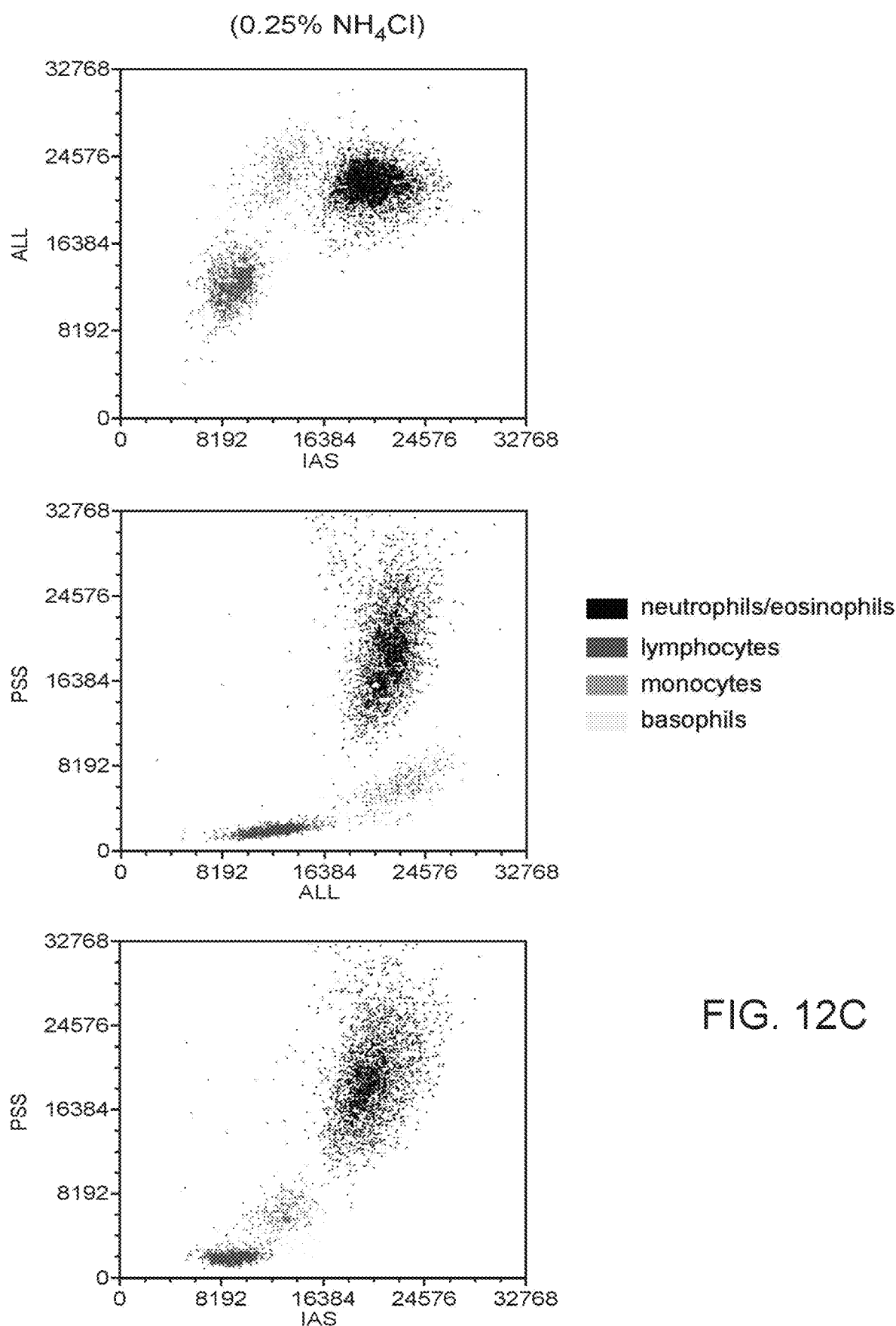
FIG. 12C shows three WBC scattergrams (ALL vs. IAS, PSS vs. ALL, and PSS vs. IAS) obtained using a WBC analysis reagent containing 0.25% ammonium chloride as an osmolality adjustment component. Neutrophils/eosinophils, lymphocytes, monocytes, and basophils are shown in the scattergrams.
Figure 12D:
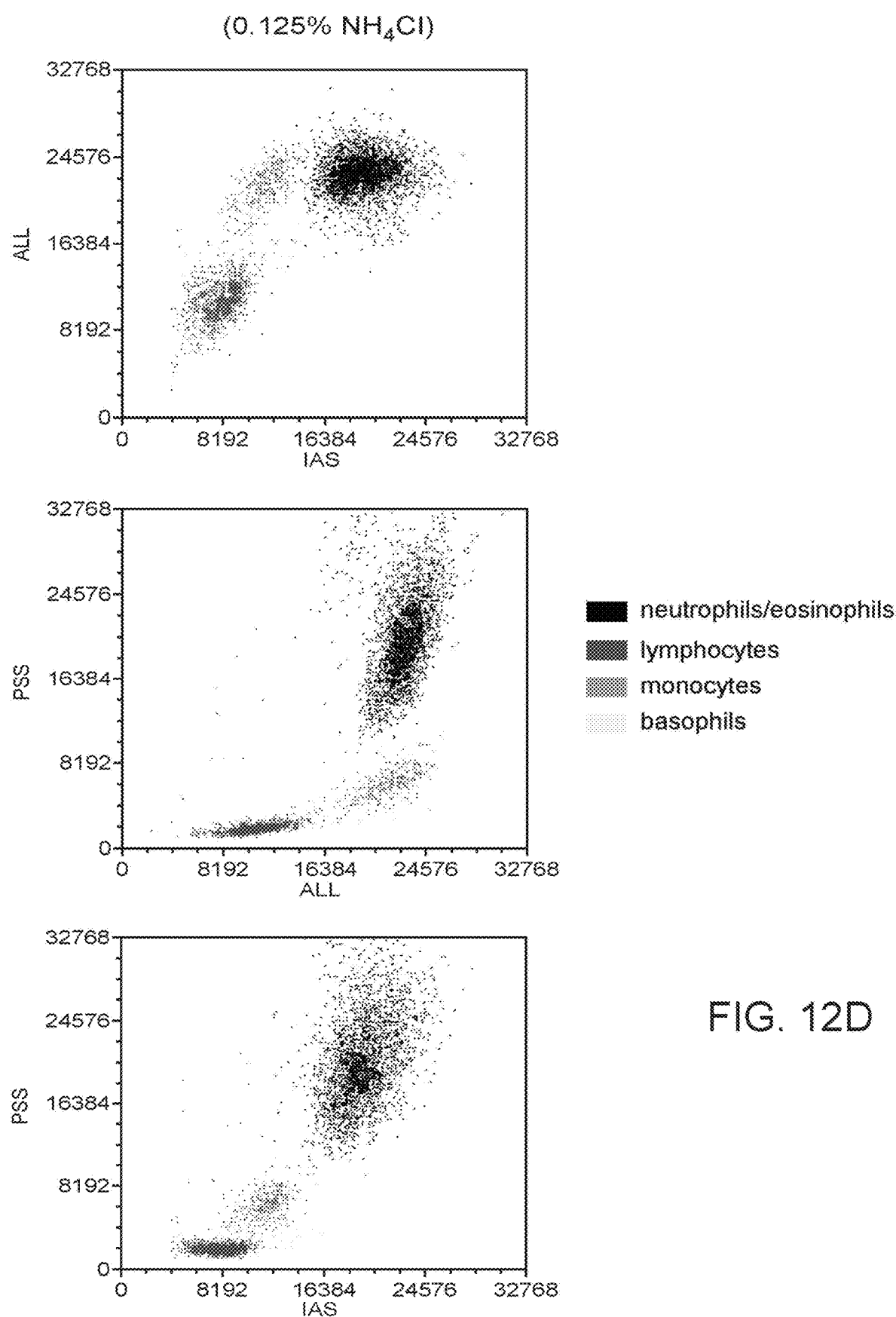
FIG. 12D shows three WBC scattergrams (ALL vs. IAS, PSS vs. ALL, and PSS vs. IAS) obtained using a WBC analysis reagent containing 0.125% ammonium chloride as an osmolality adjustment component. Neutrophils/eosinophils, lymphocytes, monocytes, and basophils are shown in the scattergrams. A comparison between FIGS. 12A-12D indicates that changes in the concentration of the ammonium chloride in the WBC analysis reagent resulted in a shift of the position of the WBC subpopulations on the scattergrams.

FIGS. 11A-11C show various WBC scattergrams of a normal whole blood specimen that was analyzed using a WBC analysis reagent containing 0.5% isopropyl alcohol as the WBC protecting agent (same formulation as Example Formulation 9).

FIGS. 12A-12D show various WBC scattergrams (ALL vs. IAS, PSS vs. ALL, and PSS vs. IAS) obtained using a WBC analysis reagent containing the indicated concentration of ammonium chloride as an osmolality adjustment component. Neutrophils/eosinophils, lymphocytes, monocytes, and basophils are shown in the scattergrams. The WBC analysis reagent had the same formulation as used in Example Formulation 10, except the concentration of ammonium chloride was adjusted as indicated. Changes in the concentration of the ammonium chloride in the WBC analysis reagent resulted in a shift of the position of the WBC subpopulations on the scattergrams. For example, the concentration of ammonium chloride was varied from 0.125% to 0.5% in the WBC reagent. The osmolality change resulting from various ammonium chloride concentration changes impacted the relative positions among neutrophils, lymphocytes and monocytes in ALL vs. IAS scattergrams. A lower concentration of ammonium chloride and lower osmolality appeared to "lift" the neutrophil population and create space for the basophils on the scattergram. The osmolalities were measured at 263, 224, 181 and 146 mOsm, respectively, for the WBC reagents containing 0.5%, 0.375%, 0.25%, and 0.125% ammonium chloride. The positional shift of the neutrophil/eosinophil population can be seen by comparing the scattergrams.

Figure 13:
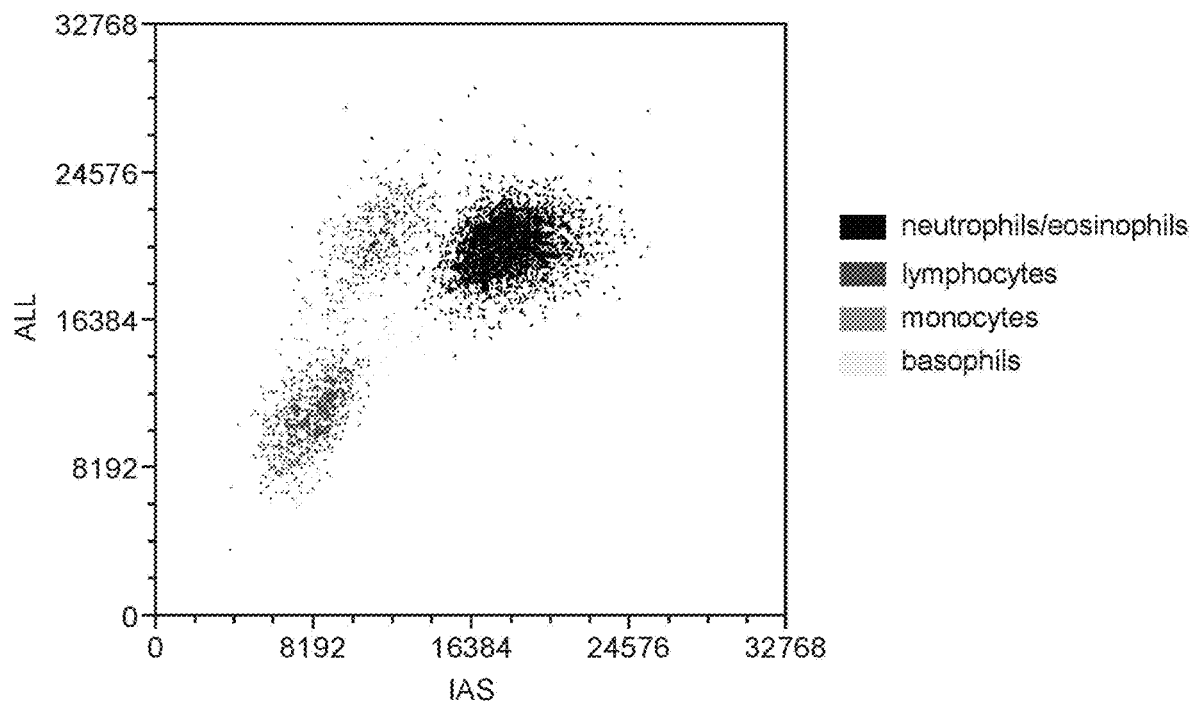
FIG. 13, Panels A-E show WBC scattergrams (ALL vs. IAS) obtained using WBC reagents containing various concentrations of sodium chloride. Panel A: no NaCl added; Panel B: +0.033% NaCl; Panel C: +0.066% NaCl; Panel D: +0.100% NaCl; Panel E: +0.133% NaCl. Neutrophils/eosinophils, lymphocytes, monocytes, and basophils are shown in the scattergrams.
Figure 13:
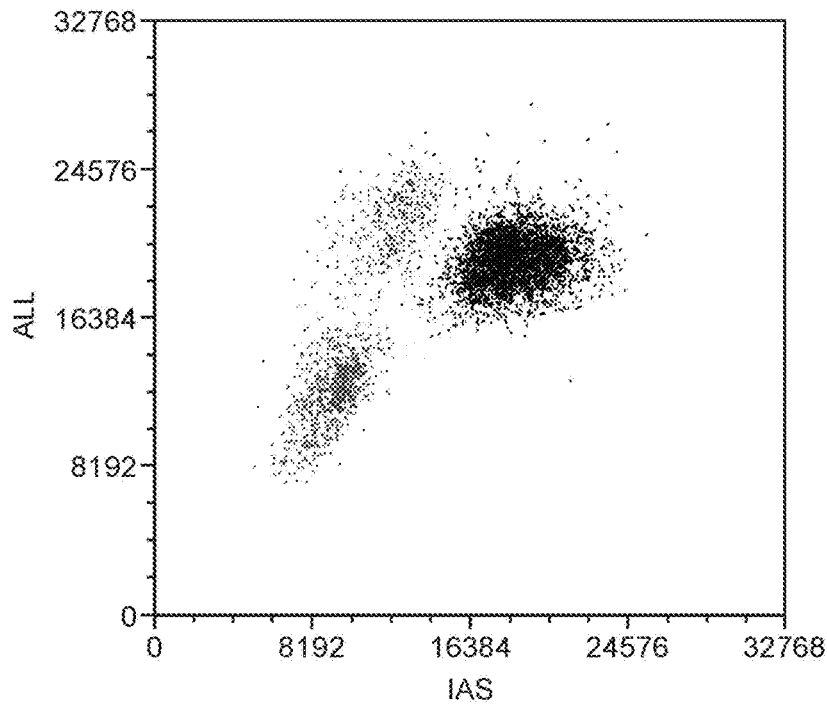
Figure 13:
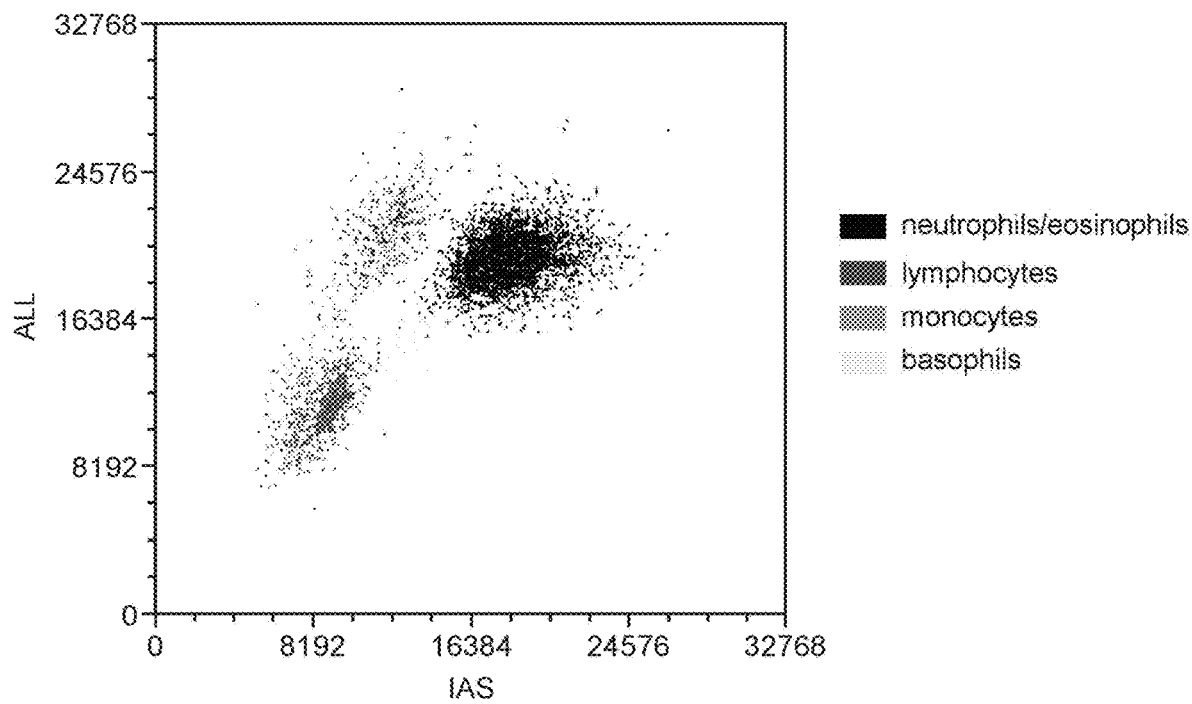
Figure 13:
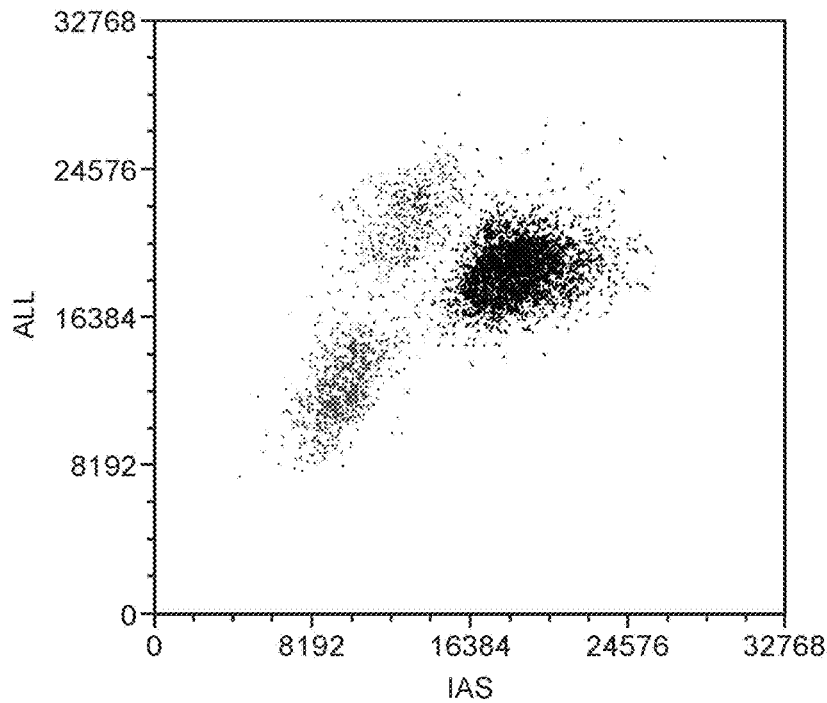
Figure 13:
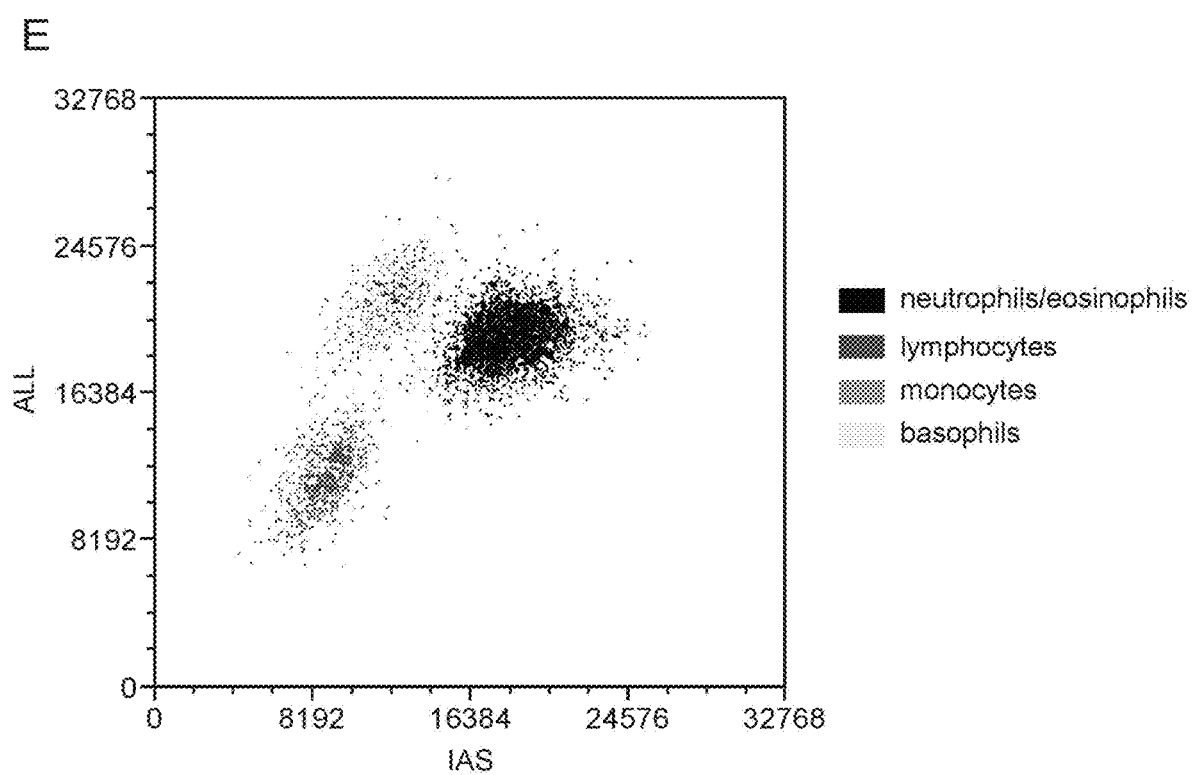

FIG. 13 shows the relative shift of WBC populations due to osmolality changes resulting from various concentrations of NaCl (see Example Formulation 11). The osmolality ranged from 149 to 181 mOsm in this experiment.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

The above Detailed Description refers to the accompanying drawings that illustrate one or more exemplary embodiments. Other embodiments are possible. Modifications may be made to the embodiment described without departing from the spirit and scope of the present invention. Therefore, the Detailed Description is not meant to be limiting. Further, the Summary and Abstract sections may set forth one or more, but not all exemplary embodiments of the present invention as contemplated by the inventor(s), and thus, are not intended to limit the present invention and the appended claims in any way.

What is claimed is:
1. A method of performing a white blood cell (WBC) analysis with an automated hematology analyzer, the method comprising:
(a) diluting a sample of whole blood with a WBC analysis reagent, wherein the WBC analysis reagent comprises:
a membrane-permeable fluorescent dye dissolved in an organic solvent, wherein the membrane-permeable fluorescent dye labels a plurality of nucleus-containing cells in the sample;
an osmolality adjustment component that separates a plurality of WBC subpopulations from one another when analyzed with the hematology analyzer, wherein the osmolality adjustment component is ammonium chloride and sodium chloride; and
a WBC protecting agent,
wherein the osmolality of the WBC analysis reagent ranges from 146 to 158 mOsm/L;
(b) incubating the diluted blood sample of step (a) for an incubation period of less than 25 seconds, at a temperature ranging from 30° C. to 50° C.;
(c) delivering the incubated sample from step (b) to a flow cell in the hematology analyzer;
(d) exciting the incubated sample from step (c) with an excitation source as the incubated sample traverses the flow cell;
(e) collecting a plurality of light scatter signals and at least one fluorescence emission signal from the excited sample; and
(f) performing a WBC differential analysis based on all the signals collected in step (e), while removing from consideration, using only a fluorescence threshold configured in the hematology analyzer, any particles within the diluted blood sample that are below the fluores- cence threshold, wherein the fluorescent threshold is based on only the at least one fluorescence emission signal.

2. The method according to claim 1, wherein the excitation source has a wavelength of from 350 nm to 700 nm.

3. The method according to claim 1, wherein the fluorescence emission signal is collected at a wavelength of from 360 nm to 750 nm by a band-pass filter or a long-pass filter.

4. The method according to claim 1, wherein the membrane-permeable fluorescent dye is acridine orange, hexidium iodide, SYTO RNA Select, SYTO 12 or SYTO 14.

5. The method according to claim 1, wherein the concentration of the membrane-permeable fluorescent dye in the reagent ranges from 0.0001% to 0.0005%.

6. The method according to claim 1, wherein the concentration of the membrane-permeable fluorescent dye in the reagent ranges from 0.01 μM to 15 μM.

7. The method according to claim 1, wherein the concentration of the osmolality adjustment component ranges from 0.1% to 0.158%.

8. The method according to claim 1, wherein the WBC protecting agent is formaldehyde, glutaraldehyde, butoxyethanol, phenoxyethanol, or isopropyl alcohol.

9. The method according to claim 1, wherein the concentration of the WBC protecting agent ranges from 0.1% to 1.0%.

10. The method according to claim 1, wherein the WBC analysis reagent further comprises a surfactant.

11. The method according to claim 10, wherein the surfactant is saponin.

12. The method according to claim 10, wherein the concentration of the surfactant ranges from 0.01% to 0.05%.

13. The method according to claim 1, wherein the reagent further comprises a pH buffering component.

14. The method according to claim 13, wherein the pH buffering component is sodium acetate or sodium bicarbonate.

15. The method according to claim 13, wherein the concentration of the pH buffering component ranges from 0.01% to 0.5%.

16. The method according to claim 1, wherein the reagent further comprises an antimicrobial agent.

17. The method according to claim 16, wherein the concentration of the antimicrobial agent ranges from 0.01% to 0.1%.

18. The method according to claim 1, wherein the pH of the WBC analysis reagent ranges from 2.5 to 12.5 pH units.

19. The method according to claim 1, wherein the osmolality of the WBC analysis reagent ranges from 149 to 158 mOsm/L.

20. The method according to claim 1, wherein the organic solvent is dimethyl sulfoxide (DMSO).

* * * * *